US012285471B2

(12) United States Patent
Lim et al.

(10) Patent No.: US 12,285,471 B2
(45) Date of Patent: Apr. 29, 2025

(54) METHODS FOR TREATING PULMONARY DISEASE USING INTER-ALPHA INHIBITOR PROTEINS

(71) Applicant: ProThera Biologics, Inc., Providence, RI (US)

(72) Inventors: Yow-Pin Lim, Providence, RI (US); Denice Spero, Providence, RI (US); Richard Andrews, Providence, RI (US)

(73) Assignee: Prothera Biologics, Inc., Providence, RI (US)

( * ) Notice: Subject to any disclaimer, the term of this patent is extended or adjusted under 35 U.S.C. 154(b) by 265 days.

(21) Appl. No.: 17/821,713

(22) Filed: Aug. 23, 2022

(65) Prior Publication Data
US 2023/0190894 A1 Jun. 22, 2023

Related U.S. Application Data

(63) Continuation of application No. 16/331,408, filed as application No. PCT/US2017/051403 on Sep. 13, 2017, now abandoned.

(60) Provisional application No. 62/394,025, filed on Sep. 13, 2016.

(51) Int. Cl.
A61K 38/55 (2006.01)
A61K 9/00 (2006.01)
A61K 38/57 (2006.01)
A61P 11/00 (2006.01)
A61P 31/04 (2006.01)
C07K 14/81 (2006.01)
A61K 45/06 (2006.01)

(52) U.S. Cl.
CPC ............ A61K 38/57 (2013.01); A61K 9/0019 (2013.01); A61K 38/55 (2013.01); A61P 11/00 (2018.01); A61P 31/04 (2018.01); C07K 14/811 (2013.01); A61K 45/06 (2013.01)

(58) Field of Classification Search
CPC ...... A61K 38/57; A61K 9/0019; A61K 38/55; A61K 45/06; A61P 31/04; A61P 11/00; C07K 14/811
See application file for complete search history.

(56) References Cited

U.S. PATENT DOCUMENTS

| | | | |
|---|---|---|---|
| 4,839,298 A | 6/1989 | Kay et al. | |
| 5,166,133 A | 11/1992 | Houston et al. | |
| 5,777,081 A | 7/1998 | Michalski et al. | |
| 5,948,894 A | 9/1999 | Berry et al. | |
| 6,069,236 A | 5/2000 | Burnout-Radosevich et al. | |
| 6,313,091 B1 | 11/2001 | Wisniewski et al. | |
| 6,489,128 B1 | 12/2002 | Lim et al. | |
| 6,660,482 B1 | 12/2003 | Lim et al. | |
| 6,673,908 B1 | 1/2004 | Stanton, Jr. | |
| 7,470,666 B2 * | 12/2008 | Fu ........................... A61P 11/00 514/1.5 |
| 7,932,365 B2 | 4/2011 | Lim et al. | |
| 7,939,282 B2 | 5/2011 | Fast et al. | |
| 9,139,641 B2 | 9/2015 | Lim et al. | |
| 9,505,814 B2 | 11/2016 | Bairstow et al. | |
| 9,572,872 B2 | 2/2017 | Lim et al. | |
| 9,758,570 B2 | 9/2017 | Lim et al. | |
| 10,076,559 B2 | 9/2018 | Lim et al. | |
| 10,258,675 B2 | 4/2019 | Lim et al. | |
| RE47,972 E | 5/2020 | Lim et al. | |
| 2003/0027848 A1 | 2/2003 | Billotte et al. | |
| 2003/0149062 A1 | 8/2003 | Jung et al. | |
| 2003/0190732 A1 | 10/2003 | Josic | |
| 2004/0009212 A1 | 1/2004 | Tsai | |
| 2006/0079670 A1 | 4/2006 | Komatsoulis et al. | |
| 2006/0110774 A1 | 5/2006 | Fast et al. | |
| 2007/0160594 A1 | 7/2007 | Filvaroff et al. | |
| 2007/0172479 A1 | 7/2007 | Warne et al. | |
| 2007/0297982 A1 | 12/2007 | Lim et al. | |
| 2010/0285507 A1 | 11/2010 | Cho et al. | |
| 2011/0038917 A1 | 2/2011 | Kappers et al. | |
| 2011/0190194 A1 | 8/2011 | Lim et al. | |
| 2011/0190208 A1 | 8/2011 | Kerstrom et al. | |
| 2011/0236381 A1 | 9/2011 | Garantziotis et al. | |
| 2011/0293594 A1 | 12/2011 | Teschner et al. | |
| 2012/0028269 A1 | 2/2012 | Lim et al. | |
| 2012/0053113 A1 | 3/2012 | Bairstow et al. | |
| 2013/0274171 A1 | 10/2013 | Fiala et al. | |
| 2014/0206844 A1 | 7/2014 | Lim | |
| 2015/0166624 A1 | 6/2015 | Tseng et al. | |

(Continued)

FOREIGN PATENT DOCUMENTS

| | | | |
|---|---|---|---|
| CN | 1972961 A | 5/2007 | |
| CN | 103889221 A | 6/2014 | |

(Continued)

OTHER PUBLICATIONS

Shorr et al. "Methicillin-resistant *Staphylococcus aureus* prolongs intensive care unit stay in ventilator-associated pneumonia, despite initially appropriate antibiotic therapy", Crit Care Med 2006, pp. 700-706 (Year: 2006).*
Leng et al. "Ulinastatin for acute lung injury and acute respiratory distress syndrome: A systematic review and meta-analysis.", World J Crit Care Med, 2014; pp. 34-41 (Year: 2014).*
Ender et al. "Pneumonia Associated with Near-Drowning", Clinical Infectious Diseases, 1997, pp. 896-907 (Year: 1997).*
Lim et al. "Correlation between Mortality and the Levels of Inter-Alpha Inhibitors in the Plasma of Patients with Severe Sepsis", The Journal of Infectious Diseases, 2003, pp. 919-926 (Year: 2003).*
McCullough et al. "Exogenous inter-a inhibitor proteins prevent cell death and improve ischemic strokes outcomes in mice", J Clin Invest, 2021, pp. 1-16 (Year: 2021).*
Cazzola et al., "Emerging anti-inflammatory strategies for COPD," Eur Respir J. 40(3):724-41 (2012).

(Continued)

*Primary Examiner* — Catherine S Hibbert
(74) *Attorney, Agent, or Firm* — Clark & Elbing LLP

(57) ABSTRACT

The invention features methods for treating or preventing pulmonary diseases, including acute respiratory distress syndrome (ARDS) and pneumonia, in a subject in need thereof that involve administering to the subject inter-alpha inhibitor proteins (IαIps), including, e.g., inter-alpha inhibitor (IαI) and/or pre-alpha inhibitor (PαI).

18 Claims, No Drawings

(56) References Cited

U.S. PATENT DOCUMENTS

| | | |
|---|---|---|
| 2015/0361127 A1 | 12/2015 | Lim |
| 2021/0393750 A1 | 12/2021 | Lim et al. |
| 2022/0099684 A1 | 3/2022 | Lim et al. |

FOREIGN PATENT DOCUMENTS

| | | |
|---|---|---|
| CN | 104507309 A | 4/2015 |
| CN | 103 142 650 B | 5/2016 |
| EP | 0367090 A1 | 5/1990 |
| EP | 2664337 A1 | 11/2013 |
| JP | H09-503775 A | 4/1997 |
| JP | 2003-40775 A | 2/2003 |
| JP | 2003-292459 A | 10/2003 |
| JP | 2005-531521 A | 10/2005 |
| JP | 2006-126216 A | 5/2006 |
| JP | 2006-520390 A | 9/2006 |
| JP | 2015-100316 A | 6/2015 |
| WO | WO 92/18160 A2 | 10/1992 |
| WO | WO 01/63280 A2 | 8/2001 |
| WO | WO 02/30983 A2 | 4/2002 |
| WO | WO 02/32406 A2 | 4/2002 |
| WO | WO 03/082247 A2 | 10/2003 |
| WO | WO 2004/082615 A2 | 9/2004 |
| WO | WO 2005/030252 A1 | 4/2005 |
| WO | WO 2005/046587 A2 | 5/2005 |
| WO | WO 2005/121163 A2 | 12/2005 |
| WO | WO 2007/038686 A2 | 4/2007 |
| WO | WO 2008/067655 A1 | 6/2008 |
| WO | WO 2009/154695 A1 | 12/2009 |
| WO | WO 2010/068308 A1 | 6/2010 |
| WO | WO-2012/119065 A2 | 9/2012 |
| WO | WO 2014/039987 A2 | 3/2014 |
| WO | WO 2014/113659 A1 | 7/2014 |
| WO | WO-2015/071402 A1 | 5/2015 |
| WO | WO-2016/138476 A1 | 9/2016 |
| WO | WO 2018/200722 A1 | 11/2018 |
| WO | WO-2020/086879 A1 | 4/2020 |
| WO | WO-2022/104282 A1 | 5/2022 |

OTHER PUBLICATIONS

Communication Pursuant to Article 94(3) and Rule 71(1) EPC in European Patent Application No. 04810367.5, dated Jun. 4, 2012 (2 pages).
Communication Pursuant to Article 94(3) EPC in European Patent Application No. 04810367.5, dated Jul. 1, 2013 (5 pages).
Communication Pursuant to Article 94(3) EPC in European Patent Application No. 04810367.5, dated May 23, 2014 (5 pages).
Communication Pursuant to Article 94(3) EPC in European Patent Application No. 09767008.7 dated Oct. 22, 2013 (7 pages).
Communication Pursuant to Article 94(3) EPC in European Patent Application No. 09767008.7, dated Apr. 28, 2016 (7 pages).
Communication Pursuant to Article 94(3) EPC for European Patent Application No. 09767008.7, dated Sep. 23, 2014 (6 pages).
Communication Pursuant to Rules 70(2) and 70a(2) EPC for European Patent Application No. 09767008.7, dated Aug. 12, 2011 (1 page).
Decision of Refusal for Japanese Patent Application No. 2011-511643, mailed Dec. 9, 2014 (4 pages).
English Translation of Notification of Reason for Refusal in Japanese Patent Application No. 2011-511643, mailed on Nov. 12, 2013 (7 pages).
English Translation of Search Report for Chinese Patent Application No. 201210460374.2, dated Aug. 22, 2014 (3 pages).
English Translation of the Notification of Reason for Refusal for Japanese Patent Application No. 2015-080358, mailed Mar. 30, 2016 (5 pages).
EPO Communication pursuant to Rule 112(1) EPC for European Patent Application No. 09767008.7, dated Aug. 11, 2015 (3 pages).
Examination Report for Australian Patent Application No. 2009260822, issued Aug. 23, 2016 (3 pages).
Extended European Search Report for European Application No. EP 09767008.7, dated Jul. 26, 2011 (7 pages).
First Office Action for Chinese Patent Application No. 200980129119.6, dated Apr. 7, 2013 (31 pages).
Fourth Office Action for Chinese Patent Application No. 200980129119.6, issued Jul. 30, 2015 (19 pages).
Fourth Office Action for Chinese Patent Application No. 201210460374.2, dated Aug. 25, 2015 (5 pages).
International Preliminary Report on Patentability and Written Opinion of the International Searching Authority for International Application No. PCT/US2009/003291, dated Nov. 30, 2010 (6 pages).
International Preliminary Report on Patentability and Written Opinion of the International Searching Authority for International Application No. PCT/US2013/058791, mailed Jun. 11, 2015 (7 pages).
International Preliminary Report on Patentability and Written Opinion of the International Searching Authority for International Application No. PCT/US2014/012033, mailed Jul. 30, 2015 (10 pages).
International Search Report and Written Opinion for International Application No. PCT/US2014/012033, mailed May 27, 2014 (14 pages).
International Search Report and Written Opinion for International Patent Application No. PCT/US2013/058791, mailed Jan. 10, 2014 (11 pages).
International Search Report for International Application No. PCT/US2004/036848, mailed Nov. 4, 2005 (5 pages).
International Search Report for International Application No. PCT/US2009/003291, mailed Aug. 24, 2009 (2 pages).
Notice of Preliminary Rejection for Korean Patent Application No. 10-2010-7029406, dated Oct. 30, 2015 (14 pages).
Office Action for Canadian Patent Application No. 2544816, dated Dec. 30, 2013 (4 pages).
Office Action for Canadian Patent Application No. 2544816, dated Mar. 1, 2012 (7 pages).
Office Action for Canadian Patent Application No. 2544816, dated Oct. 20, 2014 (6 pages).
Office Action for Canadian Patent Application No. 2726281, dated Aug. 10, 2016 (4 pages).
Office Action for Canadian Patent Application No. 2726281, dated Jun. 30, 2015 (9 pages).
Office Action for Chinese Patent Application No. 201210460374.2, dated Jan. 24, 2014 (5 pages).
Partial Supplementary European Search Report for European Application No. 14740523.7, dated Jun. 8, 2016 (7 pages).
Second Office Action for Chinese Patent Application No. 200980129119.6, issued Feb. 20, 2014 (19 pages).
Second Office Action for Chinese Patent Application No. 201210460374.2, dated Aug. 22, 2014 (11 pages).
Supplementary European Search Report for European Patent Application No. 04810367, dated Jan. 18, 2010 (7 pages).
Third Office Action for Chinese Patent Application No. 200980129119.6, issued Nov. 15, 2014 (21 pages).
Third Office Action for Chinese Patent Application No. 201210460374.2, dated Apr. 2, 2015 (5 pages).
Carter, "Potent antibody therapeutics by design," Nature Rev Immunol. 6(5):343-57 (2006).
Ge et al., "Effect observation of ulinastatin combined with high dose ambroxol in the treatment of patients with severe pneumonia," J Clin Pul Med 18(1):63-64 (2013) (4 pages).
Shah et al., "Blood Level of Inter-Alpha Inhibitor Proteins Distinguishes Necrotizing Enterocolitis From Spontaneous Intestinal Perforation," available in PMC Jan. 1, 2018, published as final edited form as: J Pediatr 180:135-140 (Jan. 2017) (16 pages).
Invitation to Pay Additional Fees for International Application No. PCT/US2019/057911, dated Dec. 26, 2019 (3 pages).
International Search Report and Written Opinion for International Application No. PCT/US2019/057911, dated Feb. 21, 2020 (29 pages).
International Search Report and Written Opinion for International Application No. PCT/US18/29436, mailed Aug. 31, 2018 (19 pages).
Chaaban et al., "The role of inter-alpha inhibitor proteins in the diagnosis of neonatal sepsis," J Pediatr. 154(4):620-622.e1 (Apr. 2009) (4 pages).

(56) References Cited

OTHER PUBLICATIONS

Chaaban et al., "Inter-(alpha) inhibitor protein and its associated glycosaminoglycans protect against histone-induced injury," Blood. 125(14):2286-96 (Apr. 2015).

Zhang et al., "Constitutive expression of inter-alpha-inhibitor (IalphaI) family proteins and tumor necrosis factor-stimulated gene-6 (TSG-6) by human amniotic membrane epithelial and stromal cells supporting formation of the heavy chain-hyaluronan (HC-HA) complex," J Biol Chem. 287(15):12433-44 (Apr. 2012).

Teiwes, Hanno, Thesis: "A Paper-Based Lateral Flow Device for the Detection of I(Alpha)IP via ELISA," Master of Science, University of Rhode Island, 2014 (134 pages).

Mizon et al., "Development of an enzyme-linked immunosorbent assay for human plasma inter-alpha-trypsin inhibitor (ITI) using specific antibodies against each of the H1 and H2 heavy chains." J Immuno Methods. 190:61-70 (Mar. 1996).

Rucevic et al., "Altered levels and molecular forms of granzyme K in plasma from septic patients." Shock 27(5):488-493 (May 2007).

"WARK PAB, DX-890 Dyax", iDrugs, vol. 5, No. 6, Jan. 1, 2002 (Jan. 1, 2002), pp. 586-589.

Adair, Jennifer E., et al. "Inter-alpha-trypsin Inhibitor Promotes Bronchial Epithelial Repair after Injury through Vitronectin Binding", Journal of Biological Chemistry, American Society for Biochemistry and Molecular Biology, US, vol. 284, No. 25, Jun. 1, 2009 (Jun. 1, 2009), pp. 16922-16930.

Ahmed et al., "Inhibition of allergic late airway responses by inhaled heparin-derived oliqosaccharides," J Aool Physiol. 88(5):1721-9 (2000).

Ahmed et al., "Prevention of exercise-induced bronchoconstriction by inhaled low-molecular-weight heparin," Am J Respir Crit Care Med. 160(2):576-81 (1999).

Atmani et al., "Role of inter-alpha-inhibitor and its related proteins in urolithiasis. Purification of an inter-alpha-inhibitor related protein from the bovine kidney," Ural Res. 27(1):57-61 (1999).

Baek et al., "Inter-alpha Inhibitor Proteins in Infants and Decreased Levels in Neonatal Sepsis," J Pediatr. 143(1):11-5 (2003).

Bauer et al., Acute Respiratory Distress Syndrome and Pneumonia: A Comprehensive Review of Clinical Data, Clinical Practice, 2006; pp. 748-756 (Year: 2006).

Bogdan et al., "Tumor necrosis factor-alpha contributes to apoptosis in hippocampal neurons during experimental group B streptococcal meningitis," J Infect Dis. 176(3):693-7 (1997).

Bove, "Anaphylactic reaction to purified anti-hemophilic factor concentrate," Transfusion 28(6):603 (1988).

Bradding et al., "TNF alpha is localized to nasal mucosal mast cells and is released in acute allergic rhinitis," Clin Exp Allergy. 25(5):406-15 (1995) (Abstract only provided) (1 paqe).

Brass et al., "Chronic LPS inhalation causes emphysema-like changes in mouse lung that are associated with apoptosis," Am J Respir Cell Mol Biol. 39(5):584-90 (2008).

Burnout, "Chromatography in plasma fractionation: benefits and future trends," J Chromatogr B Biomed Appl. 664(1):3-15 (1995).

Campo et al., "Molecular-weight-dependent effects of nonanticoagulant heparins on allergic airway responses," J Aool Physiol. 86(2):549-57 (1999).

Carrette, O et al. "Purification and characterization of pig inter-alpha-inhibitor and its constitutive heavy chains." Biochimica et biophysica acta vol. 1338,1 (1997): 21-30. doi:10.1016/s0167-4838(96)00184-7.

Carter, Paul J. "Potent antibody therapeutics by design." Nature reviews. Immunology vol. 6,5 (2006): 343-57. doi:10.1038/nri1837.

Daveau, M et al. "Human inter-alpha-inhibitor family in inflammation: simultaneous synthesis of positive and negative acute-phase proteins." The Biochemical journal vol. 292 ( Pt 2),Pt 2 (1993): 485-92. doi:10.1042/bj2920485.

De la Motte, Carol A et al. "Mononuclear leukocytes bind to specific hyaluronan structures on colon mucosal smooth muscle cells treated with polyinosinic acid:polycytidylic acid: inter-alpha-trypsin inhibitor is crucial to structure and function." The American journal of pathology vol. 163,1 (2003): 121-33. doi:10.1016/s0002-9440(10)63636-x.

Doukas, John et al. "Aerosolized phosphoinositide 3-kinase gamma/delta inhibitor TG100-115 [3-[2,4-diamino-6-(3-hydroxyphenyl)pteridin-7-yl]phenol] as a therapeutic candidate for asthma and chronic obstructive pulmonary disease." The Journal of pharmacology and experimental therapeutics vol. 328,3 (2009): 758-65. doi:10.1124/jpet.108.144311.

Emmett, M., et al. "Protein Abnormalities in Adult Respiratory Distress Syndrome, Tuberculosis, and Cystic Fibrosis Sera", Experimental Biology and Medicine, vol. 184, No. 1, Jan. 1, 1987 (Jan. 1, 1987), pp. 74-82.

Enghild, J J et al. "Analysis of inter-alpha-trypsin inhibitor and a novel trypsin inhibitor, pre-alpha-trypsin inhibitor, from human plasma. Polypeptide chain stoichiometry and assembly by glycan." The Journal of biological chemistry vol. 264,27 (1989): 15975-81.

Feldmann, Marc, and Ravinder N Maini. "Lasker Clinical Medical Research Award. TNF defined as a therapeutic target for rheumatoid arthritis and other autoimmune diseases." Nature medicine vol. 9,10 (2003): 1245-50. doi:10.1038/nm939.

Fries, Erik, and Aneta Kaczmarczyk. "Inter-alpha-inhibitor, hyaluronan and inflammation." Acta biochimica Polonica vol. 50,3 (2003): 735-42.

Garantziotis, Stavros et al. "Inter-alpha-trypsin inhibitor attenuates complement activation and complement-induced lung injury." Journal of immunology (Baltimore, Md. : 1950) vol. 179,6 (2007): 4187-92. doi:10.4049/jimmunol.179.6.4187.

Garantziotis, Stavros, et al. "Serum Inter-[alpha]-Trypsin Inhibitor and Matrix Hyaluronan Promote Angiogenesis in Fibrotic Lung Injury", American Journal of Respiratory and Critical Care Medicine, vol. 178, No. 9, Nov. 1, 2008 (Nov. 1, 2008), pp. 939-947.

Hamm et al., "Frequent expression loss of Inter-alpha-trypsin inhibitor heavy chain (ITIH) genes in multiple human solid tumors: a systematic expression analysis," BMC Cancer. 8:25 (2008).

Hoffer et al., "Improved virus safety and purity of a chromatographically produced Factor IX concentrate by nanofiltration," J Chromatoqr B Biomed Aool. 669(2): 187-96 (1995).

International Preliminary Report on Patentability for International Application No. PCT/US17/51403, mailed Mar. 28, 2019 (16 paqes).

International Search Report and Written Opinion for International Application No. PCT/US17/51403, mailed Jan. 23, 2018 (24 paqes).

Ito et al., "A pilot randomized trial of a human anti-interleukin-6 receptor monoclonal antibody in active Crohn's disease," Gastroenteroloqy_ 126(4):989-96 (2004).

Iwasaki et al., "TNF-alpha contributes to the development of allergic rhinitis in mice," J Allergy Clin Immunol. 112(1):134-40 (2003).

Josic et al., "Proteomic characterization of inter-alpha inhibitor proteins from human plasma," Proteomics. 6(9):2874-85 (2006).

Jourdain et al., "Effects of Inter-alpha-inhibitor in Experimental Endotoxic Shock and Disseminated Intravascular Coaqulation," Am J Respir Crit Care Med. 156(6):1825-33 (1997).

Katoh et al., "Galectin-9 inhibits CD44-hyaluronan interaction and suppresses a murine model of allerqic asthma," Am J Respir Crit Care Med. 176(1):27-35 (2007).

Katz, Jeffry A. "Advances in the medical therapy of inflammatory bowel disease." Current opinion in gastroenterology vol. 18,4 (2002): 435-40. doi:10.1097/00001574-200207000-00007.

Keshari et al. A Novel C5 Complement Inhibitor Protects Against Sepsis-Induced Activation of Complement, Coagulation and Inflammation and Provides Survival Benefit in *E.coli* Sepsis, Blood, 2014, p. 112 (Year: 2014).

Koraka et al., "Plasma levels of inter-alpha inhibitor proteins in children with acute Dengue virus infection," PLoS One. 5(4):e9967 (2010) (4 paqes).

Kricka, L J. "Human anti-animal antibody interferences in immunological assays." Clinical chemistry vol. 45,7 (1999): 942-56.

Kuus-Reichel et al., "Will immunogenicity limit the use, efficacy, and future development of therapeutic monoclonal antibodies?" Clin Diaqn Lab Immunol. 1(4):365-72 (1994).

(56) References Cited

OTHER PUBLICATIONS

Leng, Yu-Xin, "Ulinastatin for acute lung injury and acute respiratory distress syndrome: A systematic review and meta-analysis", World Journal of Critical Care Medicine, vol. 3, No. 1, Jan. 1, 2014 (Jan. 1, 2014), p. 34.
Lim et al., "Affinity purification and enzymatic cleavage of inter-alpha inhibitor proteins using antibody and elastase immobilized on CIM monolithic disks," J Chromatogr A. 1065(1):39-43 (2005).
Lim et al., "Correlation between mortality and the levels of inter-alpha inhibitors in the plasma of patients with severe sepsis," J Infect Dis. 188(6):919-26 (2003).
Lim, "Inter-alpha inhibitors: From laboratory to market," <http://www.brownenterpriseforum.org/matriarch/documents/Lim.pdf>, retrieved Jul. 13, 2011 (6 pages).
Ljung et al., "Infliximab in inflammatory bowel disease: clinical outcome in a population based cohort from Stockholm County," Gut. 53(6):849-53 (2004).
Martinez-Salas et al., "Inhibition of allergic airway responses by inhaled low-molecular-weight heparins: molecular-weight dependence," J Appl Physiol. 84(1):222-8 (1998).
Mascelli et al., "Molecular, biologic, and pharmacokinetic properties of monoclonal antibodies: impact of these parameters on early clinical development," J Clin Pharmacol. 47(5):553-65 (2007).
McCann, Karl B et al. "Evaluation of expanded bed adsorption chromatography for extraction of prothrombin complex from Cohn Supernatant I." Biologicals : journal of the International Association of Biological Standardization vol. 36,4 (2008): 227-33. doi:10.1016/j.biologicals.2008.01.002.
MEGA- and GIGA preps of cosmid-, BAC-, PAC, YAC-, and P1-DNA with JETSTAR 2.0, Sep. 2005 (6 paqes).
Michalski et al., "Preparation and properties of a therapeutic inter-alpha-trypsin inhibitor concentrate from human plasma," Vox Sanq. 67(4):329-36 (1994).
Mihara et al., "IL-6/IL-6 receptor system and its role in physiological and pathological conditions," Clin Sci (Land). 122(4):143-59 (2012).
Mizon et al., "Human pre-alpha-inhibitor: isolation from a by-product of industrial scale plasma fractionation and structural analysis of its H3 heavy chain," J Chromatogr B Biomed Sci Appl. 692(2):281-91 (1997).
Mo, J-H et al. "Anti-tumor necrosis factor-alpha treatment reduces allergic responses in an allergic rhinitis mouse model." Allergy vol. 66,2 (2011): 279-86. doi:10.1111/j.1398-9995.2010.02476.x.
Molinari et al., "Inhibition of antigen-induced airway hyperresponsiveness by ultralow molecular-weiaht heparin," Am J Resoir Crit Care Med. 157(3 Pt 1):887-93 (1998).
Odum, "Inter-alpha-trypsin inhibitor and pre-alpha-trypsin inhibitor in health and disease. Determination by immunoelectrophoresis and immunoblotting," Biol Chem Hoppe Seyler. 371(12):1153-8 (1990).
Opal et al., "Inter-alpha-inhibitor proteins are endogenous furin inhibitors and provide protection against experimental anthrax intoxication," Infect Immun. 73(8):5101-5 (2005).
Opal et al., "Longitudinal studies of inter-alpha inhibitor proteins in severely septic patients: a potential clinical marker and mediator of severe sepsis," Crit Care Med. 35(2):387-92 (2007).
ProThera Biologics, "Inter-alpha Inhibitor Proteins (IAIP): Protein Replacement Therapy to Treat Systemic Inflammation," Oct. 2010, retrieved from <http://www.ri-bizplan.com/Portals/O/Uploads/Documents/Resources/ProThera.pdf> (12 pages).
Raoust, Eloïse et al. "Pseudomonas aeruginosa LPS or flagellin are sufficient to activate TLR-dependent signaling in murine alveolar macrophages and airway epithelial cells." PloS one vol. 4,10 e7259. Oct. 6, 2009, doi:10.1371/journal.pone.0007259.
Rui, Meng, et al."Urinary Trypsin Inhibitor Attenuates Seawater-Induced Acute Lung Injury by Influencing the Activities of Nuclear Factor-KB and Its Related Inflammatory Mediators", Respiration, vol. 83, No. 4, Jan. 1, 2012 (Jan. 1, 2012), pp. 335-343.
Rutgeerts et al., "Optimizing anti-TNF treatment in inflammatory bowel disease," Gastroenterology_ 126(6):1593-610 (2004).
Salier et al., "Purification of the human serum inter-alpha-trypsin inhibitor by zinc chelate and hydrophobic interaction chromatomaohies," Anal Biochem. 109(2):273-83 (1980).
Salier, J P et al. "Inter-alpha-trypsin-inhibitor (ITI): use of immunoadsorbents for preparation of anti-ITI antiserum, ITI-free human serum and purified ITI." Journal of immunological methods vol. 47,2 (1981): 239-48. doi:10.1016/0022-1759(81)90124-1.
Salier, J P et al. "The inter-alpha-inhibitor family: from structure to regulation." The Biochemical journal vol. 315 ( Pt 1),Pt 1 (1996): 1-9. doi:10.1042/bj3150001.
Sanon et al., "Peripheral arterial ischemic events in cancer patients," Vase Med. 16(2):119-30 (2011).
Saukkonen et al., "The role of cytokines in the generation of inflammation and tissue damage in experimental gram-positive meningitis," J Exp Med. 171(2):439-48 (1990).
Simones et al. "Antibiotic resistance patterns of group B streptococcal clinical isolates", Infect Dis Obstet Gynecol 2004; 12: 1-8 ( Year: 2004).
Sin et al., "Chronic obstructive pulmonary disease as a risk factor for cardiovascular morbidity and mortality," Proc Am Thorac Soc. 2(1):8-11 (2005).
Singh et al. "Inter-Alpha Inhibitor Protein Administration Improves Survival From Neonatal Sepsis in Mice", Pediatric Research, 2020, pp. 242-247 (Year: 2010).
Singh, Kultar et al. "Inter-alpha inhibitor protein administration improves survival from neonatal sepsis in mice." Pediatric research vol. 68,3 (2010): 242-7. doi:10.1203/PDR.0b013e3181e9fdf0.
Su, Xiao et al. "Role of CFTR expressed by neutrophils in modulating acute lung inflammation and injury in mice." Inflammation research : official journal of the European Histamine Research Society . . . [et al.] vol. 60,7 (2011): 619-32. doi:10.1007/s00011-011-0313-x.
Sykes, Megan, and Boris Nikolic. "Treatment of severe autoimmune disease by stem-cell transplantation." Nature vol. 435,7042 (2005): 620-7. doi:10.1038/nature03728.
Takeuchi, Tsutomu et al. "Baseline tumour necrosis factor alpha levels predict the necessity for dose escalation of infliximab therapy in patients with rheumatoid arthritis." Annals of the rheumatic diseases vol. 70,7 (2011): 1208-15. doi:10.1136/ard.2011.153023.
Tanaka et al., "Targeting interleukin-6: all the way to treat autoimmune and inflammatory diseases," IntJ Biol Sci. 8(9):1227-36 (2012).
Tarner et al., "Treatment of autoimmune disease by adoptive cellular gene therapy, " Ann NY Acad Sci. 998:512-9 (2003).
Trefz, G et al. "Establishment of an enzyme-linked immuno-sorbent assay for urinary trypsin inhibitor by using a monoclonal antibody." Journal of immunoassay vol. 12,3 (1991): 347-69. doi:10.1080/01971529108055077.
Triantaphyllopoulos et al., "A model of chronic inflammation and pulmonary emphysema after multiple ozone exposures in mice," Am J Physiol Luna Cell Mol Physiol. 3OO(5):L691-7OO (2011).
Van Heel, David A et al. "Inflammatory bowel disease is associated with a TNF polymorphism that affects an interaction between the OCT1 and NF(-kappa)B transcription factors." Human molecular genetics vol. 11,11 (2002): 1281-9. doi:10.1093/hmg/11.11.1281.
Verhein et al., "IL-1 receptors mediate persistent, but not acute, airway hyperreactivity to ozone in guinea pigs," Am J Respir Cell Mol Biol. 39(6):730-8 (2008).
Wu et al., "Delayed administration of human inter-alpha-inhibitor (IaI) reduces mortality in sepsis," Critical Care. 197(3S):S41 (2003) (Abstract Only).
Wu, Rongqian et al. "Delayed administration of human inter-alpha inhibitor proteins reduces mortality in sepsis." Critical care medicine vol. 32,8 (2004): 1747-52. doi:10.1097/01.ccm.0000132903.14121.0e.
Yang et al., "Administration of human inter-alpha-inhibitors maintains hemodynamic stability and improves survival durinq sepsis," Crit Care Med. 30(3):617-22 (2002).
Yan-Lei, Ge, et al. "Effect observation of ulinastatin combined with high dose ambroxol in the treatment of patients with severe pneumonia", Journal of Clinical Pulmonary Medicine, vol. 18, No. 1, Jan. 1, 2013 (Jan. 1, 2013), pp. 63-64.

(56) References Cited

OTHER PUBLICATIONS

Yan-Lei, Ge, et al. "Observation of the efficacy of ulinastatin combined with high-dose ambroxol in the treatment of severe pneumonia", Journal of Clinical Pulmonary Medicine, vol. 18, No. 1, Jan. 1, 2013 (Jan. 1, 2013), pp. 63-64.
Zhuo et al., "Defect in SHAP-hyaluronan complex causes severe female infertility. A study by inactivation of the bikunin qene in mice," J Biol Chem. 276(11):7693-6 (2001) (5 paqes).
Zosky et al., "Animal models of asthma," Clin Exp Allergy. 37(7):973-88 (2007).
Communication Pursuant to Article 94(3) EPC in European Patent Application No. 19876409.4, dated Feb. 1, 2024 (5 pages).
Communication Pursuant to Article 94(3) EPC in European Patent Application No. 19876409.4, dated Jun. 27, 2023 (15 pages).
English Translation of Office Action for Israeli Patent Application No. 270069, dated Jun. 7, 2023 (6 pages).
English Translation of Office Action for Japanese Patent Application No. 2021-523071, dated Sep. 4, 2023 (3 pages).
English Translation of Second Office Action for Chinese Patent Application No. 201880027257.2, issued Jul. 26, 2023 (7pages).
Extended European Search Report for European Application No. EP 19876409.4, dated Aug. 3, 2022 (22 pages).
Hatayama et al., "High-mobility group box-1 and inter-alpha inhibitor proteins: In vitro binding and co-localization in cerebral cortex after hypoxic-ischemic injury," FASEB J. 35(3):e21399 (Mar. 2021) (16 pages).
Herrmann K. and Carroll K., "An Exclusively Human Milk Diet Reduces Necrotizing Enterocolitis," Breastfeeding Medicine. 9(4):184-190 (2014) (7 Pages).
Htwe et al., "Inter-[alpha] inhibitor proteins maintain neutrophils in a resting state by regulating shape and reducing ROS production," Blood Adv. 2(15):1923-34 (Aug. 2018).
International Preliminary Report on Patentability and Written Opinion of the International Searching Authority for International Application No. PCT/US2021/059569, issued May 16, 2023 (7 pages).
International Search Report and Written Opinion for PCT/US2021/059569, dated Mar. 30, 2022 (15 pages).
Kanwar et al., "Comparative activities of milk components in reversing chronic colitis," J. Dairy Sci. 99(4):2488-2501 (Apr. 2016) (14 pages).
Lee et al., "Heparin immobilized gold nanoparticles for targeted detection and apoptotic death of metastatic cancer cells," Biomaterials. 31(25):6530-6 (Sep. 2010) (Abstract Only).
Muheem et al., "A review on the strategies for oral delivery of proteins and peptides and their clinical perspectives," Saudi Pharmaceutical Journal 24:413-428 (Jun. 2014) (16 pages).
Opstelten et al., "Dairy Products, Dietary Calcium, and Risk of Inflammatory Bowel Disease: Results From a European Prospective Cohort Investigation," Inflamm Bowel Dis. 22(6):1403-1411 (Jun. 2016) (9 pages).
Pankhurst et al., "Characterization of the heparin-binding properties of human clusterin," Biochemistry. 37(14):4823-30 (Apr. 1998).
Radmacher et al., "Milk as a Vehicle for Oral Medications: Hidden Osmoles," J. Perinatology 32:227-229 (2012) (4 pages).
Song et al., "Metals in protein-protein interfaces," Annu Rev Biophys. 43:409-31 (2014) (25 pages).
Spasova et al., "Ischemia Reduces Inter-Alpha Inhibitor Proteins in the Brain of the Ovine Fetus," available in PMC Jun. 1, 2018. Published in final form as Dev Neurobiol. 77(6):726-737 (Jun. 2017) (19 pages).
Threlkeld et al., "Effects of inter-alpha inhibitor proteins on neonatal brain injury: Age, task and treatment dependent neurobehavioral outcomes," Experimental Neurology 261:424-433 (Jul. 2014) (10 pages).

* cited by examiner

METHODS FOR TREATING PULMONARY DISEASE USING INTER-ALPHA INHIBITOR PROTEINS

CROSS-REFERENCE TO RELATED APPLICATIONS

This application is a continuation of U.S. application Ser. No. 16/331,408, filed Mar. 7, 2019, which is a National Stage of International Patent Application No. PCT/US2017/051403 filed Sep. 13, 2017, which claims priority to U.S. Provisional Application No. 62/394,025 filed Sep. 13, 2016, the entire contents of which are incorporated herein for all purposes by this reference.

FIELD OF THE INVENTION

The present invention relates to the treatment of acute pulmonary disease, including acute respiratory distress syndrome (ARDS) and pneumonia.

BACKGROUND

Acute respiratory distress syndrome (ARDS) is a critical illness characterized by acute lung injury leading to pulmonary edema and respiratory failure. Patients that have experienced trauma, hemorrhage, severe pneumonia, influenza, and/or sepsis are at risk of developing ARDS. Despite significant advances in critical care management, mortality from ARDS remains over 40%. Each year over 100,000 people are estimated to die from complications of ARDS in the United States.

Pneumonia is a common but critical illness characterized by inflammation of the lungs, which most often results from an infection of the lungs. There are over 450 million reported cases of pneumonia and an estimated 4 million deaths resulting from pneumonia each year. Pneumonia is particularly severe among children, the elderly, and patients with chronic disease. Pneumonia can be further classified in terms of location of onset, such as community-acquired or hospital-acquired pneumonia. Community-acquired pneumonia occurs in approximately 1.3 million individuals in the United States each year.

The inflammatory process in the lung that is associated with ARDS and pneumonia is a major contributor to the progression of disease and its adverse outcomes. Current therapy for ARDS and pneumonia focuses on treating the cause of the injury or disease, such as by administration of antibiotics for infection, and therapy also focuses on treating disease related symptoms, such as fluid accumulation and associated reductions in oxygen transport in the alveoli.

There exists a need in the art for improved methods for treating acute pulmonary diseases such as ARDS and pneumonia, for treating the associated inflammatory process, and for improving the tissue repair process in the lung.

SUMMARY OF THE INVENTION

The invention features methods for treating and preventing acute respiratory distress syndrome (ARDS) and pneumonia in a subject in need thereof by administering inter-alpha inhibitor proteins (IαIps), for example, IαI and/or PαI, to the subject.

In a first aspect, the invention features a method of treating or reducing the likelihood of developing acute respiratory distress syndrome (ARDS) or pneumonia in a subject in need thereof including administering to the subject inter-alpha inhibitor proteins (IαIps).

In several embodiments of the first aspect of the invention, the IαIps include IαI, PαI, a heavy chain, a light chain, or a combination thereof. In some embodiments, the IαIps include IαI, PαI, and/or bikunin. In some embodiments, the IαIps include IαI and/or PαI. In some embodiments, the IαIps include IαI and PαI. In some embodiments, the heavy chain is selected from the group consisting of H1, H2, H3, H4, and H5. In some embodiments, the light chain is bikunin.

In several embodiments of the first aspect of the invention, the ARDS or the pneumonia is caused by an infection caused by bacteria. In some embodiments, the bacteria are antibiotic resistant bacteria.

In several embodiments of the first aspect of the invention, the method extends a treatment period prior to development of sepsis or organ failure in the subject, relative to an untreated subject.

In several embodiments of the first aspect of the invention, the method includes treating one or more symptoms of the ARDS including mild, moderate or severe hypoxemia as determined by Partial Pressure of arterial oxygen/Fraction of inspired oxygen ($PaO_2/FiO_2$) or positive end-expiratory pressure (PEEP), bilateral opacities, respiratory failure, shortness of breath, labored breathing, cough, fever, increased heart rate, low blood pressure, confusion, extreme tiredness, rapid breathing, organ failure, chest pain, bluish coloring of nails or lips, an change in the level of one or more inflammatory markers, or need for mechanical ventilation. In some embodiments, the one or more inflammatory markers is selected from the group consisting of TNF-alpha, IL-6, C5a, DAMPs, ERK, NF-κB, IL-10, and a serine protease and combinations thereof. In some embodiments, the change in the level of one or more inflammatory markers is an increase, e.g., relative to a healthy subject. In other embodiments, the change in the level of one or more inflammatory markers is a decrease, e.g., relative to a healthy subject.

In several embodiments of the first aspect of the invention, the subject has one or more symptoms of ARDS including shortness of breath, cough, fever, rapid heart rate, low blood pressure, rapid breathing, chest pain, bluish coloring of nails, or bluish coloring of lips.

In several embodiments of the first aspect of the invention, the ARDS is acute respiratory failure (ARF).

In several embodiments of the first aspect of the invention, the ARDS results from sepsis, pneumonia, ventilation induced pneumonia, trauma, damage to the brain, a blood transfusion, babesiosis, lung contusion, lung transplant, aspiration of stomach contents, drug abuse, drug overdose, a burn, pancreatitis, near drowning, inhalation of chemical fumes, or administration of resuscitation fluid. In some embodiments, the chemical fumes are selected from the group consisting of smoke, phosgene, chlorine gas, acrolein, ammonia, ethylene oxide, formaldehyde, hydrogen chloride, hydrogen fluoride, hydrogen sulfide, methyl bromide, sodium azide, sulfur dioxide, cadmium fume, mercury fume, mustard gas, nickel carbonyl, oxides of nitrogen, ozone. In some embodiments, the ARDS results from sepsis. In some embodiments, the sepsis is infectious sepsis or sterile sepsis. In some embodiments, the resuscitation fluid includes colloid solutions. In some embodiments, the colloid solution includes hydroxyethyl starch solution. In some embodiments, the colloid solution includes albumin. In some embodiments, the trauma is acidosis.

In several embodiments of the first aspect of the invention, the method includes treating one or more symptoms of the pneumonia including symptoms included in the CRB-65 test, the CURB-65 test, or the pneumonia severity index (PSI), cough, fever, shaking chills, shortness of breath, wheezing, chest pain, headache, excessive sweating, clammy skin, loss of appetite, low energy, fatigue, confusion, muscle pain, or muscle weakness.

In several embodiments of the first aspect of the invention, the subject has one or more symptoms of pneumonia including cough, fever, shaking chills, shortness of breath, wheezing, chest pain, headache, excessive sweating, clammy skin, loss of appetite, low energy, fatigue, confusion, muscle pain, muscle weakness, or inflammation.

In several embodiments of the first aspect of the invention, the pneumonia is hospital-acquired pneumonia (HAP), health care-associated pneumonia (HCAP), nursing home-acquired pneumonia (NHAP), ventilator-associated pneumonia (VAP), or community-acquired pneumonia (CAP). In some embodiments, the CAP is severe CAP (sCAP).

In several embodiments of the first aspect of the invention, the pneumonia results from an infection of lung tissue. In some embodiments, the infection is a bacterial infection, a viral infection, a fungal infection, a parasite infection, or an infection caused by another type of microorganism. In some embodiments, the bacterial infection is caused by an *Enterobacteriaceae* species (spp.), *Streptococcus pneumoniae*, *Staphylococcus aureus*, *Bacillus anthracis*, *Haemophilus influenzae*, *Klebsiella pneumoniae*, *Escherichia coli*, *Pseudomonas aeruginosa*, *Bordetella pertussis*, *Moraxella catarrhalis*, *Coxiella burnetii*, *Chlamydophila pneumoniae*, a *Legionella* spp., or *Mycoplasma pneumoniae*. In some embodiments, the *Staphylococcus aureus* is methicillin-resistant *Staphylococcus aureus* (MRSA). In some embodiments, the *Legionella* species is *Legionella pneumonophila*. In some embodiments, the viral infection is caused by an influenza virus, parainfluenza, swine origin influenza, Respiratory syncytial virus, Human parainfluenza virus, an Adenovirus, a Metapneumovirus, Severe acute respiratory syndrome virus, herpes simplex virus (HSV), Varicella-zoster virus (VZV), measles virus, Rubella virus, Cytomegalovirus (CMV), smallpox virus, dengue virus, rhinovirus, bocavirus, or Middle East respiratory syndrome virus. In some embodiments, the influenza virus is an influenza virus A or an influenza virus B. In some embodiments, the fungal infection is caused by *Histoplasma capsulatum*, *Coccidioides immitis*, *Coccidioides posadasii*, *Pneumocystis jirovecii*, *Blastomyces dermatitidis*, *Sporothrix schenckii*, *Cryptococcus neoformans*, *Cryptococcus gattii*, *Paracoccidioides brasiliensis*, a *Candida* spp., an *Aspergillus* spp., or a *Mucor* spp.

In several embodiments of the first aspect of the invention, the symptoms (e.g., of the ARDS or the pneumonia) begin within 2 to 72 hours after a lung insult. In some embodiments, the lung insult is or is caused by sepsis, pneumonia, ventilation-induced pneumonia, trauma, damage to the brain, a blood transfusion, babesiosis, lung contusion, lung transplant, aspiration of stomach contents, drug abuse, drug overdose, a burn, pancreatitis, near drowning, inhalation of chemical fumes, lung transplant, a large volume of fluid used during post-trauma resuscitation, or infection of lung tissue. In some embodiments, the lung insult is or is caused by sepsis. In some embodiments, the sepsis is infectious sepsis or sterile sepsis. In some embodiments, the chemical fumes are selected from the group consisting of smoke, phosgene, acrolein, ammonia, ethylene oxide, formaldehyde, hydrogen chloride, hydrogen fluoride, hydrogen sulfide, methyl bromide, sodium azide, sulfur dioxide, cadmium fume, mercury fume, mustard gas, nickel carbonyl, oxides of nitrogen, ozone or chlorine gas.

In several embodiments of the first aspect of the invention, the method includes reducing inflammation and/or promoting repair in lung tissue.

In several embodiments of the first aspect of the invention, the method includes reducing fluid in lung tissue. In some embodiments, the lung tissue is alveolar lung tissue.

In several embodiments of the first aspect of the invention, the method includes administering I$\alpha$Ips to the subject prior to development of sepsis in the subject.

In several embodiments of the first aspect of the invention, the method includes administering I$\alpha$Ips to the subject prior to organ failure in the subject.

In several embodiments of the first aspect of the invention, the method includes measuring the levels of I$\alpha$Ips in a biological sample derived from the subject prior to administration of the I$\alpha$Ips. In some embodiments, the method includes measuring the levels of I$\alpha$I, P$\alpha$I, a heavy chain (e.g., H1, H2, H3, H4, H5, or combinations thereof), a light chain, or a combination thereof. In some embodiments, the method includes measuring the levels of I$\alpha$I, P$\alpha$I, and/or bikunin. In some embodiments, the method includes measuring the levels of I$\alpha$I and/or P$\alpha$I. In some embodiments, the method includes measuring the levels of I$\alpha$I and P$\alpha$I.

In several embodiments of the first aspect of the invention, the method includes measuring the levels of histones or histone/I$\alpha$I/P$\alpha$I complexes in a biological sample derived from the subject.

In several embodiments of the first aspect of the invention, the subject exhibits decreased levels of I$\alpha$I and/or P$\alpha$I relative to a healthy subject. In some embodiments, the level of I$\alpha$I and/or P$\alpha$I of a healthy subject is about 300 mg/L to about 1000 mg/L of circulating I$\alpha$I and/or P$\alpha$I.

In several embodiments of the first aspect of the invention, the subject exhibits increased levels of histones relative to a healthy subject.

In several embodiments of the first aspect of the invention, the subject exhibits increased levels of histone/I$\alpha$I/P$\alpha$I complexes relative to an untreated subject.

In several embodiments of the first aspect of the invention, the method includes restoring or exceeding the level of I$\alpha$I and/or P$\alpha$I in the lung tissue of the subject to that of a healthy subject. In some embodiments, the level of I$\alpha$I and/or P$\alpha$I of a healthy subject is about 300 mg/L to about 1000 mg/L of circulating I$\alpha$I and/or P$\alpha$I.

In several embodiments of the first aspect of the invention, the method includes administering a single dose or multiple doses of the I$\alpha$Ips sufficient to restore or exceed the level of the I$\alpha$Ips in the lung tissue of the subject. In some embodiments, the single dose includes about 1 mg/kg to about 50 mg/kg.

In several embodiments of the first aspect of the invention, the method further includes measuring the level of one or more biomarkers associated with the ARDS or the pneumonia in a biological sample derived from the subject.

In several embodiments of the first aspect of the invention, the one or more biomarkers include histone, histone/P$\alpha$I complexes, histone/I$\alpha$I complexes, histone I$\alpha$I/P$\alpha$I complexes, TNF-$\alpha$, IL-6, IL-10, IL-1, IL-1ra, IL1B, IL-8, MCP-1, MIP-2, CRP, PCT, cytokine-induced neutrophil chemoattractant/KC, UTI, a complement component, or fragments thereof. In some embodiments, the complement component is selected from the group consisting of C1, C2, C3, C3a, C3b, C4, C4b, C5, C5a, C5b, C6, C7, C8, C9, membrane attack complex, Factor B, Factor D, MASP-1, and MASP-2.

In several embodiments of the first aspect of the invention, the biological sample derived from the subject is a blood sample, a urine sample, a sputum sample, or a bronchiolar lavage fluid sample. In some embodiments, the blood sample is whole blood, serum, plasma, or a combination thereof.

In several embodiments of the first aspect of the invention, the method further includes administering a second treatment for the ARDS or the pneumonia. In some embodiments, the second treatment includes one or more of an antibiotic, an antiviral agent, an antifungal agent, an anti-parasitic agent, an anti-inflammatory agent, a bronchodilator, a vasopressor, a sedative, or mechanical ventilation.

In several embodiments of the first aspect of the invention, the method further includes administering an inhibitor of complement activation.

In several embodiments of the first aspect of the invention, the method includes neutralization of histones and extracellular histones.

In several embodiments of the first aspect of the invention, the administration of the IαIps inhibits activation of one or more complement components. In some embodiments, the complement components include C1, C2, C3, C3a, C3b, C4, C4b, C5, C5a, C5b, C6, C7, C8, C9, membrane attack complex, Factor B, Factor D, MASP-1, MASP-2, or fragments thereof.

In several embodiments of the first aspect of the invention, the administration of the IαIps reduces the likelihood of death or hospitalization time for the subject.

In several embodiments of the first aspect of the invention, the method includes administering a composition including IαIps (e.g., IαI and/or PαI). In some embodiments, the method includes administering a composition including IαI and/or PαI. In some embodiments, the method includes administering a composition including IαI and PαI. In some embodiments, the composition includes a dosage of IαI and/or PαI of about 1 mg/kg to about 50 mg/kg. In some embodiments, the composition includes a dosage of the IαI and/or PαI of about 5 mg/kg to about 15 mg/kg. In some embodiments, the composition is administered to the subject one or more times every 1, 2, 3, 4, 5, 6, 8, 12, or 24 hours, every 1, 2, 3, 4, 5, or 6, days, or every 1, 2, 3, or 4 weeks. In some embodiments, the composition further includes a pharmaceutically acceptable excipient, diluent, or carrier. In some embodiments, the composition is formulated as a solid. In some embodiments, the composition is formulated as a liquid. In some embodiments, the composition is formulated for inhalation, insufflation, nebulization, or injection, or is formulated for oral, rectal, topical, or intraperitoneal administration. In some embodiments, the injection is intravenous injection. In some embodiments, the composition has a half-life of greater than 1, 1.5, 2, 2.5, 3, 3.5, 4, 4.5, 5, 7.5, or 10 hours. In some embodiments, the composition further includes an antibiotic, an antiviral agent, an antifungal agent, an anti-parasitic agent, an anti-inflammatory agent, a vasopressor, a sedative, or a bronchodilator. In some embodiments, the antibiotic agent includes amoxicillin, penicillin, doxycycline, clarithromycin, benzylpenicillin, azithromycin, daptomycin, linezolid, levofloxacin, moxifloxacin, gatifloxcin, gentamicin, macrolides, cephalosporins, azithromycin, ciprofloxacin, cefuroxime, amoxillin-potassium clavulanate, erythromycin, sulfamethoxazole-trimethoprim, doxycycline monohydrate, cefepime, ampicillin, cefpodoxime, ceftriaxone, cefazolin, erythromycin ethylsuccinate, meropenem, piperacillin-tazobactam, amikacin, erythromycin stearate, cefepime in dextrose, doxycycline hyclate, ampicillin-sulbactam, ceftazidime, gemifloxacin, gentamicin sulfate, erythromycin lactobionate, imipenem-cilastatin, cefoxitin, cefditoren pivoxil, ertapenem, doxycycline-benzoyl peroxide, ampicillin-sulbactam, meropenem, cefuroxime, cefotetan, or piperacillin-tazobactam. In some embodiments, the antiviral agent includes zanamivir, oseltamivir, permivir, ribavirin, acyclovir, ganciclovir, foscarnet, or cidofovir. In some embodiments, the antifungal agent includes amphotericin, caspofungin, voriconazole, itraconazole, posaconazole, fluconazole, or flucytosine. In some embodiments, the antiparasitic agent includes nitazoxanide, melarsoprol, eflornithine, metronidazole, tinidazole, miltefosine, mebendazole, pyrantel pamoate, thiabendazole, diethylcarbamazine, ivermectin, albendazole, praziquantel, or rifampin. In some embodiments, the anti-inflammatory agent includes a corticosteroid, a statin, a steroid, a nonsteroidal anti-inflammatory drug, or a glucocorticoid. In some embodiments, the bronchodilator includes a beta 2 agonist, a xanthine, ipratropium, oxitropium, a muscarinic receptor antagonist, ipratropium, oxitropium, theophylline, theobromine, caffeine, salbutamol, isoproterenol, albuterol, levalburerol, pirbuterol, metaproterenol, terbutaline, salmeterol, or formoterol. In some embodiments, the vasopressor includes epinephrine, isoproterenol, phenylephrine, norepinephrine, dobutamine, ephedrine, or droxidopa. In some embodiments, the sedative includes propofol, diprivan, morphine, fentanyl, midazolam, lorazepam, precede, infumorph, dexmedetomidine, or alfentanil. In some embodiments, the composition further includes an inhibitor of complement activation. In some embodiments, the composition inhibits activation of one or more complement components. In some embodiments, the complement components include C1, C2, C3, C4, C5, or fragments thereof.

In several embodiments of the first aspect of the invention, the subject is a mammal. In some embodiments, the mammal is human. In some embodiments, the human is an infant, a child, or an adult. In particular, the subject is a child or is an adult at or above the age of 65 years old. In some embodiments, the mammal is a horse, a dog, a cat, a rabbit, or a pig. In some embodiments, the subject has the ARDS or the pneumonia.

In several embodiments of the first aspect of the invention, the subject is not hospitalized. In other embodiments, the subject is hospitalized. In some embodiments, the subject is in an intensive care unit.

In several embodiments of the first aspect of the invention, the subject requires ventilator-assisted breathing. In some embodiments, the ventilator-assisted breathing is mechanical ventilator-assisted breathing. In some embodiments, the mechanical ventilator-assisted breathing is invasive mechanical ventilator-assisted breathing. In some embodiments, the mechanical ventilator-assisted breathing is non-invasive mechanical ventilator-assisted breathing. In some embodiments, the mechanical ventilator-assisted breathing is pressure-limited or volume-limited.

In several embodiments of the first aspect of the invention, the subject has one or more organ failures. In some embodiments, the subject has two or more organ failures. In some embodiments, the subject has failures of the liver failure, kidney, intestine, heart, or brain. In some embodiments, the subject has respiratory failure.

In several embodiments of the first aspect of the invention, the subject is identified as being in need of treatment using one or more of the following: chest imaging, arterial blood gas level, partial pressure of oxygen ($PaO_2$) levels, partial pressure of carbon dioxide ($PaCO_2$) levels, blood pH, pathogen specific test, or sputum evaluation. In some embodiments, the chest imaging is chest X-ray.

In several embodiments of the first aspect of the invention, the subject is identified as having mild, moderate or severe hypoxemia as determined by $PaO_2/FiO_2$ or positive end-expiratory pressure (PEEP).

In several embodiments of the first aspect of the invention, the subject is identified as having bilateral opacities consistent with edema.

In several embodiments of the first aspect of the invention, the subject is identified as having confusion, blood urea nitrogen being equal to one more than 20 mg/dL, respiratory rate being equal to or greater than 30 breaths per minute, systolic blood pressure being less than 90 mm Hg, diastolic blood pressure being equal to or less than 60 mm Hg, or is 65 or older.

In several embodiments of the first aspect of the invention, the subject is identified as being a nursing home resident; having neoplastic disease; having a history of liver, heart, cerebrovascular, or renal disease; being in a state of altered mental state; having a respiratory rate greater than or equal to 30 breaths per minute; having a systolic blood pressure above 90 mmHg, having a temperature above 35° C. or greater than or equal to 40° C.; having a pulse greater than or equal to 125/min; arterial pH less than 7.35; having a blood urea nitrogen greater than or equal to 30 ng/dL, sodium levels being greater than 130 mmol/L; having glucose levels greater than or equal to 250 mg/dl or greater than 13.8 mmol/liter); having hematocrit values being less than 30%; having a partial pressure of oxygen less than 60 mm Hg; or by the presence of pleural effusion on X-ray.

In several embodiments of the first aspect of the invention, the administration of the IαIps reduces the physiological response to inflammatory mediators such as cytokines, chemokines, complement, or histones.

In several embodiments of the first aspect of the invention, the subject has undergone a lung transplant. In some embodiments, the subject is scheduled to undergo a lung transplant.

In several embodiments of the first aspect of the invention, the method includes administering the IαIps (e.g., IαI and/or PαI) to the subject at least 10, 15, 20, 30, 60, or 120 minutes after a lung insult. In some embodiments, the lung insult occurs as a result of radiation treatment, chemotherapy, or exposure to high altitude, swimming, or diving.

In several embodiments of the first aspect of the invention, the method includes administering the IαIps (e.g., IαI and/or PαI) to the subject at least 10, 15, 20, 30, 60, or 120 minutes before a lung insult. In some embodiments, the lung insult occurs as a result of surgery.

In several embodiments of the first aspect of the invention, the IαIps (e.g., IαI and/or PαI) are administered at physiological proportions.

In several embodiments of the first aspect of the invention, the IαIps (e.g., IαI and/or PαI) are at about 80% to about 100% purity (e.g., about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% purity).

Definitions

As used herein, the term "acute respiratory distress syndrome" or "ARDS" refers to an acute form of lung injury characterized by widespread inflammation of the lungs that may include, for example, diffuse alveolar injury, surfactant dysfunction, an innate immune response, and/or abnormal coagulation. ARDS is also typically characterized by bilateral pulmonary infiltrates and severe hypoxemia in the absence of evidence for cardiogenic pulmonary edema. The severity of hypoxemia necessary to make the diagnosis of ARDS can be defined by the ratio of the partial pressure of oxygen in the patient's arterial blood ($PaO_2$) to the fraction of oxygen in the inspired air ($FiO_2$) ($PaO_2/FiO_2$). A definition of ARDS depends on the relationship of the timing of the onset of clinical symptoms to the lung injury, radiographic changes, origin of edema, and severity of the symptoms based on the measurement of $PaO_2/FiO_2$ ratio on 5 cm of $H_2O$ continuous positive airway pressure (CPAP). The 2012 Berlin definition for ARDS classified ARDS into three categories based on the degree of hypoxemia as determined by $PaO_2/FiO_2$: mild ARDS ($PaO_2/FiO_2$ 200-300 mm Hg), moderate ARDS ($PaO_2/FiO_2$ 100-200 mm Hg), and severe ARDS ($PaO_2/FiO_2 \leq 100$ mm Hg) (see, e.g., The ARDS Definition Task Force, *JAMA* 307(23):2526-2533, 2012). The American-European Consensus Conference on ARDS (AECC) classified ARDS in terms of a $PaO_2/FiO_2$ ratio of less than 200 mm Hg, whereas acute lung injury (ALI), which is less severe than ARDS, was characterized by a $PaO_2/FiO_2$ of less than 300 mm Hg (Bernard et al., *Am. J. Respir. Crit. Care Med.* 143(3 Pt 1):818-824, 1994). It is to be understood that the term "ARDS" encompasses any suitable clinical definition for ARDS known in the art, including the 2012 Berlin definition or the 1994 AECC definition.

As used herein, the term "acute respiratory failure" refers to a condition in which fluid builds up in the air sacs of the lung, thereby reducing the release of oxygen into the blood stream (hypoxemia) and removal of $CO_2$ (hypercapnia) and leading to a hypoxic condition in the subject. The hypoxic condition can reduce oxygen delivery to organs, which can result in organ failure. Failure to remove $CO_2$ from blood can result in respiratory acidosis characterized by an increase in blood pH.

As used herein, the term "community-acquired pneumonia" or "CAP" refers to pneumonia acquired by a patient outside a hospital or long-term care facility. While CAP can occur in a patient of any age, CAP is typically considered a disease predominantly of the elderly, with incidence rising steeply above about 70 years of age. In patients above 65 years of age, CAP can be associated with more severe disease and fewer of the classical symptoms such as fever and chest pain as compared to younger patients. CAP-associated mortality is greatest within about the first 5 days of hospitalization.

As used herein, the term "complement activation" refers to the activation of complement components that react with one another to induce a series of inflammatory responses that help to fight infection. The complement system activates through a triggered-enzyme cascade.

As used herein, the term "complement components" refers to complement system proteins in the classical pathway, lectin pathway, and the alternate complement pathways, including but not limited to C1, C2, C3 (e.g., C3a and C3b), C4 (e.g., C4b), C5 (e.g., C5a and C5b), C6, C7, C8, C9, membrane attack complex, Factor B, Factor D, mannan-binding lectin associated serine protease 1 (MASP-1), and MASP-2, and fragments thereof.

The term "health care-associated pneumonia" or "HCAP" refers to a pneumonia that includes patients who have been hospitalized within about 90 days of the infection, resided in a nursing home or long-term care facility (which is referred to herein as "nursing home-acquired pneumonia" or "NHAP"), or received parenteral antimicrobial therapy, chemotherapy, or wound care within about 30 days of onset of pneumonia. NHAP is currently the largest subgroup of HCAP. NHAP is associated with a relatively high mortality rate, which may in part be due to the fact that patients are typically older, have greater comorbidity, and more severe functional impairment than a typical CAP patient.

As used herein, the term "hospital-acquired pneumonia" refers to a pneumonia contracted by a patient while present in a medical facility such as a hospital. Hospital-acquired pneumonia may be contracted by a patient, for example, at least about 48-72 hours after being admitted to a hospital.

As used herein, the term "inter-alpha inhibitor proteins" or "IαIps" refers to large, multi-component glycoproteins in a family of structurally related serine protease inhibitors. IαIps have been shown to be important in the inhibition of an array of proteases including neutrophil elastase, plasmin, trypsin, chymotrypsin, Granzyme K, preprotein convertase, furin, cathepsin G, and acrosin. In human plasma, IαIps are found at relatively high concentrations (400-800 mg/L). Unlike other inhibitor molecules, this family of inhibitors typically includes a combination of polypeptide chains (light and heavy chains) covalently linked by a chondroitin sulfate chain. The heavy chains of IαIps (H1, H2, and H3) are also called hyaluronic acid (HA) binding proteins. The major forms of IαIps found in human plasma are inter-alpha-inhibitor (IαI), which contains two heavy chains (H1 and H2) and a single light chain (L), and pre-alpha-inhibitor (PαI), which contains one heavy (H3) and one light chain (L). Another IαIp is the light chain (also termed bikunin (bi-kunitz inhibitor) with two Kunitz domains), which is known to broadly inhibit plasma serine proteases. Another IαIp is the heavy chain-related molecule H4, which circulates in the blood without linkage to bikunin. Yet another IαIp is the heavy chain-related molecule H5. IαI and PαI present in the plasma fraction have an apparent molecular weight of between about 60 kDa to about 280 kDa.

As used herein, the term "pneumonia" refers to an inflammatory condition in the lung which is the result of an infection caused by bacteria, viruses, fungi, or other microorganisms such as parasites (e.g., protozoan parasites). Pneumonia is typically diagnosed with chest X-rays, by clinical assessments, sputum culture, and/or blood culture. In a patient having pneumonia, the air sacs fill with fluid (e.g., pus) and may become solid. The infection and related inflammation may affect both lungs, one lung, or only certain lobes of a lung. The term "pneumonia" encompasses any suitable clinical definition or classification of pneumonia known in the art, for example, the CRB-65 criteria, CURB-65 criteria (see, e.g., Lim et al., *Thorax* 58(5):377-382, 2003) or the pneumonia severity index (PSI) (see, e.g., Fine et al., *N. Engl. J. Med.* 336(4):243-250, 1997). These criteria are also described in Wente et al. *Respiratory Medicine* 109:157-169, 2015, which is incorporated herein by reference in its entirety. The term pneumonia encompasses any suitable type of pneumonia, including but not limited to hospital-acquired pneumonia (HAP), health care-associated pneumonia (HCAP), nursing home-acquired pneumonia (NHAP), ventilator-associated pneumonia (VAP), and community acquired pneumonia (CAP), including severe CAP (sCAP).

As used herein, the phrase "reducing fluid in lung tissue" refers to a decrease in the volume of fluid in the lungs using, e.g., a method such as aspiration, administration of a therapeutic (e.g., a diuretic or a heart medication), or surgery to reduce excess fluid in lungs. The reduction may be relative to a reference or a control treatment (e.g., a placebo or a reference therapeutic agent). The reduction may also be relative to a volume of fluid in a subject prior to onset of treatment, or at a time point following treatment.

As used herein, the phrase "reducing the likelihood of developing" refers to prophylactic treatment of a patient who susceptible to, or otherwise at risk of, a particular disease, syndrome, or condition (e.g., the conditions described herein, such as acute pulmonary disease (e.g., ARDS or pneumonia)) or is at risk of a current disease, syndrome, or condition increasing in its degree of severity, for example, a patient having CAP who is at risk of progressing to severe community acquired pneumonia (sCAP).

As used herein, the term "respiratory failure" refers to a condition resulting from inadequate gas exchange by the respiratory system in which insufficient oxygen passes from the lungs into blood and $CO_2$ is expelled.

As used herein, the term "sepsis" refers to a systemic response to an infection (referred to herein as "infectious sepsis") or to a non-infectious process associated with acute tissue injury and innate immune activation (referred to interchangeably herein as "sterile inflammation" or "sterile sepsis"), which can lead to tissue damage, organ failure, and death. Infectious sepsis can result from an infection caused by bacteria, viruses, fungi, or other microorganisms such as parasites (e.g., protozoan parasites). Sterile sepsis can occur after hemorrhagic shock, polytrauma, pancreatitis, transplant rejection, autoimmune disease, or ischemia/reperfusion and is not associated with the presence of a known infection.

As used herein, the term "severe community acquired pneumonia" or "sCAP" refers to a type of CAP wherein the patients require admission to the intensive care unit. In some cases, a patient with sCAP may have septic shock and/or acute respiratory failure, which may require intubation and mechanical ventilation.

As used herein, the term "subject" refers to a mammal, including, but not limited to, a human or non-human mammal, such as a primate, bovine, equine, porcine, ovine, feline, or canine. The subject may be a patient.

As used herein, the term "treating" refers to reducing or ameliorating a disorder and/or symptoms associated therewith. It will be appreciated that, although not precluded, treating a disorder or condition does not require that the disorder or symptoms associated therewith be completely eliminated.

As used herein the term "ventilator-assisted breathing" refers to non-spontaneous breathing through the assistance of a machine that assists the patient to exchange $O_2$ and $CO_2$ in the lungs.

The term "ventilator-associated pneumonia" or "VAP" refers to a pneumonia that occurs in subjects who are undergoing ventilator-assisted breathing.

DETAILED DESCRIPTION OF THE INVENTION

The invention features methods of treating subjects having or at risk of ARDS and/or pneumonia and methods of reducing the likelihood of progression of a disease (e.g., ARDS and/or pneumonia) in a subject in need thereof by administering inter-alpha inhibitor proteins (IαIps), for example, IαI and/or PαI, to the subject.

Patient Population

The invention provides methods of treating subjects that present with ARDS, pneumonia, or symptoms thereof. The invention also provides methods of reducing the likelihood of developing ARDS or pneumonia in subjects that are susceptible or prone to developing ARDS or pneumonia, for example, due to a predisposition or an expected insult, such as physical trauma or exposure to an infective agent.

Subjects suitable for treatment using the methods of the invention are those identified as having ARDS or pneumonia. These subjects may be further diagnosed as having a subcategory of ARDS or pneumonia. A subject that has ARDS may have, for example, acute respiratory failure (ARF). A subject that has pneumonia may have, for example, hospital-acquired pneumonia (HAP), healthcare-associated pneumonia (HCAP), ventilator-associated pneumonia (VAP), nursing home-associated pneumonia (NHAP), or community-acquired pneumonia (CAP), such as severe community-acquired pneumonia (sCAP).

A subject may have clinical, specific, or non-specific symptoms or signs of ARDS or pneumonia. Non-limiting examples of clinical symptoms of ARDS include one or more of the following: the presence of dyspnea; tachypnea; hypoxemia; respiratory failure; presentation with a ratio of partial pressure of arterial oxygen to fraction of inspired oxygen ($PaO_2/FiO_2$) of about 300 mm Hg or less (e.g., about 300 mm Hg, about 250 mm Hg, about 225 mm Hg, about 200 mm Hg, about 175 mm Hg, about 150 mm Hg, about 125 mm Hg, about 100 mm Hg, about 75 mm Hg, or about 50 mm Hg); the presence of unilateral or bilateral infiltrates on frontal chest radiograph; a measured level of pulmonary artery wedge pressure of 18 mm Hg or less, or no clinical evidence of left atrial hypertension. Additional non-limiting examples of ARDS symptoms include shortness of breath (e.g., severe shortness of breath), cough, fever, increased heart rate, rapid breathing, chest pain (e.g., chest pain during inhalation), and bluish coloring of nails or lips.

A medical professional may diagnose clinical pneumonia to determine if the subject is suitable for treatment using the methods of this invention by assessing the subject using the parameters included in CRB-65 criteria, the CURB-65 criteria and/or the pneumonia severity index (PSI). These criteria are described, for example, in Welte et al. *Respiratory Medicine* 109:157-169, 2015; see, e.g., Table 2.

The parameters assessed in the CRB-65 criteria include one or more of the following: confusion, respiratory rate, systolic blood pressure, diastolic blood pressure, and age. The subject scores one point each for the presence of the following clinical factors: confusion (defined as an abbreviated mental test score (AMTS) of 8 or less), respiratory rate being equal to or greater than 30 breaths per minute, systolic blood pressure being less than 90 mm Hg or diastolic blood pressure being equal to or less than 60 mm Hg, and being 65 years of age or older. Depending on how the subject scores on the CRB-65 criteria (i.e., from 1 to 4), the physician can determine the severity of pneumonia, with a score of 1 being the least severe form of pneumonia and a score of 4 being the most severe form of pneumonia.

The parameters assessed in the CURB-65 criteria include one or more of the following: confusion, blood urea nitrogen level, respiratory rate, systolic blood pressure, diastolic blood pressure, and age. The subject scores one point each for the presence of the following clinical factors: confusion (defined as an abbreviated mental test score (AMTS) of 8 or less), blood urea nitrogen greater than 7 mmol/l, respiratory rate being equal to or greater than 30 breaths per minute, systolic blood pressure being less than 90 mm Hg or diastolic blood pressure being equal to or less than 60 mm Hg, and being 65 years of age or older. Depending on how the subject scores on the CURB-65 criteria (i.e., from 1 to 5), the physician can determine the severity of pneumonia, with a score of 1 being the least severe form of pneumonia and a score of 5 being the most severe form of pneumonia.

The PSI factors may also be used to diagnose pneumonia and to determine its severity. The PSI index includes a total of 20 parameters (3 demographic, 5 comorbid conditions, 5 physical examination findings, and 7 laboratory or imaging variables). Any combination of the PSI factors may be used to diagnose pneumonia and/or determine its severity. Non-limiting examples of PSI factors that increase the severity of pneumonia include being a nursing home resident, being under 5 years of age, having neoplastic disease, having a history of disease (e.g., liver disease, congestive heart failure, cerebrovascular disease, or renal disease), being in an altered mental state, and laboratory findings (e.g., one or more of a respiratory rate greater than or equal to 30 breaths per minute, systolic blood pressure above 90 mmHg, temperature above 35° C. or greater than or equal to 40° C., pulse greater than or equal to 125/min, arterial pH less than 7.35, blood urea nitrogen greater than or equal to 30 ng/dL, sodium levels being greater than 130 mmol/L, glucose levels being greater than or equal to 250 mg/dl (US) or greater than 13.8 mmol/liter (SI), hematocrit values being less than 30%, partial pressure of oxygen being less than 60 mm Hg, and presence of pleural effusion on X-ray). The factors used to determine the severity of pneumonia may be weighed and scored differently according to approaches known in the art.

A medical professional may use the severity criteria developed by the American Thoracic Society (ATS) to diagnose sCAP. Non-limiting examples ATS factors that increase the severity of community acquired pneumonia are having a respiratory rate above 30 breaths per minute, a $PaO_2/FiO_2$ equal to or above 250 mm Hg, multilobar infiltrates, confusion and/or disorientation, uremia (e.g., BUN level greater than or equal to 20 mg/dL), leukopenia (e.g., WBC count of less than $4 \times 10^9$ cells/L), thrombocytopenia (e.g., platelet count being less than $100 \times 10^9$ cells), hypothermia (e.g., core temperature being less than 36° C.), hypotension, receiving invasive mechanical ventilation, or being in need of vasopressors.

In addition to the presence of conditions such as prior disease history and laboratory findings, a subject may be diagnosed as having pneumonia based on the presence of one or more additional symptoms. Non-limiting examples of such additional symptoms of pneumonia include one or more of cough, fever, shaking chills, shortness of breath, wheezing, chest pain (e.g. stabbing chest pain that gets worse when the subject breathes deeply, or when the subject coughs), headache, excessive sweating, clammy skin, loss of appetite, low energy (e.g., fatigue), confusion, muscle pain, or muscle weakness.

In addition to the diagnostic tools and symptoms described above, a variety of clinical diagnostic tools may also be used to diagnose ARDS and pneumonia in a subject. Non-limiting examples of such clinical diagnostic tools include one or more of chest X-ray, arterial blood gas level, partial pressure of carbon dioxide ($PaCO_2$) level, blood pH, sputum evaluation, bronchoscopy, and others known in the art.

The underlying physiological reason causing the subject to develop ARDS or pneumonia may be an infection (e.g., a bacterial infection, a viral infection, a fungal infection, or an infection by another type of microorganism (e.g., a parasite, such as a protozoan parasite)). There are many different types of bacteria, viruses, fungi, and/or other microorganisms (e.g., parasites) that can infect a subject. Determining the type of microorganism that is causing the infection associated with ARDS or pneumonia (e.g., using a pathogen-specific test) can be useful, as the type of treatment(s), for example, type of therapeutic agent (e.g., antibiotic agent) suitable for the subject may be determined accordingly.

Non-limiting examples of bacteria that can cause a bacterial infection that may lead to, exacerbate, or occur as a result of ARDS or pneumonia include, e.g., *Enterobacteriaceae* species (spp.), *Streptococcus pneumoniae*, *Staphylococcus aureus* (e.g., methicillin-resistant *S. aureus* (MRSA)), *Bacillus anthracis*, *Haemophilus influenzae*, *Klebsiella pneumoniae*, *Escherichia coli*, *Pseudomonas aeruginosa*, *Bordetella pertussis*, *Moraxella catarrhalis*, *Coxiella burnetii*, *Chlamydophila pneumoniae*, *Mycoplasma pneumoniae*, *Legionella* spp., *Legionella pneumophila*, gram negative bacteria, gram positive bacteria, and others known in the art. Cardiac disease, cerebrovascular disease, age of greater than 65 years, and nursing home residency have been shown to be independent risk factors for infection by *Enterobacteriaceae*. The bacteria causing an infection can be sensitive to common antibiotics or can be antibiotic-resistant. In some cases, relatively uncommon pathogens such as gram negative bacteria and MRSA may be resistant to first-line empirical antibiotic treatment.

Non-limiting examples of antibiotic-resistant bacteria include *Clostridium difficile*, carbapenem-resistant *Enterobacteriaceae*, *Neisseria gonorrhoeae*, multidrug-resistant *Acinetobacter*, drug-resistant *Campylobacter*, fluconazole-resistant *Candida*, extended spectrum *Enterobacteriaceae*, vancomycin-resistant *Enterococcus*, multidrug-resistant *Pseudomonas aeruginosa*, drug-resistant non-typhoidal *Salmonella*, drug-resistant *Salmonella* serotype *typhi*, drug-resistant *Shigella*, methicillin-resistant *Staphylococcus aureus* (MRSA), drug-resistant *Streptococcus pneumoniae*, drug-resistant *Tuberculosis*, vancomycin-resistant *Staphylococcus aureus*, erythromycin-resistant Group A *Streptococcus*, and clindamycin-resistant Group B *Streptococcus*.

Non-limiting examples of viruses that can cause a viral infection that may lead to, exacerbate, or occur as a result of ARDS or pneumonia include, e.g., Influenza virus A, Influenza virus B, parainfluenza, swine origin influenza, Respiratory syncytial virus, Human parainfluenza viruses, Adenoviruses, Metapneumovirus, Severe acute respiratory syndrome virus, herpes simplex virus (HSV), Varicella-zoster virus (VZV), measles virus, Rubella virus, Cytomegalovirus (CMV), smallpox virus, dengue virus, rhinovirus, bocavirus, Middle East respiratory syndrome virus, and others known in the art. Determining the kind of virus that is causing the infection associated with ARDS or pneumonia (e.g., using a pathogen-specific test) can be important as the type of treatment (e.g., the antiviral agent) suitable for the subject may be determined accordingly. Mortality due to viral pneumonia may be similar to that associated with bacterial pneumonia.

Non-limiting examples of fungi that can cause a fungal infection that may lead to, exacerbate, or occur as a result of ARDS or pneumonia include *Candida* spp. (e.g., *Candida albicans*), *Aspergillus* spp., *Mucor* spp., *Histoplasma capsulatum*, *Coccidioides immitis*, *Coccidioides posadasii*, *Pneumocystis jirovecii*, *Blastomyces dermatitidis*, *Sporothrix schenckii*, *Cryptococcus neoformans*, *Cryptococcus gattii*, *Paracoccidioides brasiliensis*, *Aspergillus* species, *Mucor* species and others known in the art. Determining the kind of fungus that is causing the infection associated with ARDS or pneumonia (e.g., using a pathogen-specific test) can be important as the type of treatment (e.g., the type of antifungal agent) suitable for the subject may be determined accordingly.

Subjects that have not yet developed ARDS or pneumonia, but that might be susceptible to developing ARDS or pneumonia due to an expected insult (e.g., trauma or exposure to an infective agent), are also suitable for treatment using the methods of this invention. Non-limiting examples of such subjects are those who have undergone a lung transplant or are scheduled to undergo a lung transplant.

In particular, the subject to be treated according to the methods described herein is a mammal, such as a human (e.g., an infant, a child, or an adult human). The subject may also be a non-human mammal, such as a horse, a dog, a cat, a rabbit, or a pig.

If the subject is in distress, they may be hospitalized (e.g., in an intensive care unit). Alternatively, the subject may be stable, and thus treatable in an outpatient clinic or in their home.

The subject may have spontaneous breathing that is inadequate to maintain life. Such subjects may require artificial ventilation in order to assist with or to replace spontaneous breathing. This may involve treatment with a mechanical ventilator. A mechanical ventilator may operate in two different modes. The first mode is positive pressure ventilation, where air is pushed into the trachea of the subject. The second mode is negative pressure ventilation, where air is sucked into the lungs. A mechanical ventilator operating in either the first mode or the second mode can be used in the context of the invention. The mechanical ventilator-assisted breathing may be pressure-limited or volume-limited. Treatment with a mechanical ventilator may occur before or after treatment of the subject with an I$\alpha$Ip (e.g., I$\alpha$I and/or P$\alpha$I) according to the methods of treatment described below.

If the subject is left untreated or if their treatment is not effective, ARDS or pneumonia can lead to organ failure and sepsis. The sepsis may be infectious sepsis or sterile sepsis. Sterile sepsis can also lead to ARDS and organ failure. Noninfectious stimuli including mechanical trauma, ischemia, toxins, minerals, crystals, chemicals, and antigens can trigger inflammation resulting in sterile sepsis. Organ failure involves organ dysfunction to such a degree that normal homeostasis cannot be maintained without external clinical intervention. The organ failure may involve liver failure, kidney failure, intestine failure, heart failure, or brain failure, for example. The subject may have respiratory failure. A subject having ARDS or pneumonia that develops organ failure or sepsis (e.g., infectious sepsis or sterile sepsis) can be treated by administering I$\alpha$Ips (e.g., I$\alpha$I and/or P$\alpha$I) and/or a composition that includes I$\alpha$Ips (e.g., I$\alpha$I and/or P$\alpha$I) according to the methods described herein.

Additionally subjects suitable for treatment using the methods of the invention include subjects with an acute lung injury or insult that develops into ARDS or pneumonia. Non-limiting examples of such insults or injuries include sepsis (including infectious sepsis and sterile sepsis), systemic inflammatory response syndrome (SIRS), pneumonia, ventilation-induced pneumonia, trauma, a blood transfusion, babesiosis, lung contusion, aspiration of stomach contents, drug abuse, drug overdose, a burn, pancreatitis, near drowning, inhalation of a chemical agent (e.g., chemical fumes, for example, chemical fumes selected from the group consisting of smoke, phosgene, acrolein, ammonia, ethylene oxide, formaldehyde, hydrogen chloride, hydrogen fluoride, hydrogen sulfide, methyl bromide, sodium azide, sulfur dioxide, cadmium fume, mercury fume, mustard gas, nickel carbonyl, oxides of nitrogen, ozone and chlorine gas), lung transplant, administration of a large volume of fluid used during post-trauma resuscitation, infection of lung tissue, surgery, radiation treatment, chemotherapy, exposure to high altitude, swimming, or diving. In some cases, the sepsis is infectious sepsis. In other cases, the sepsis is sterile sepsis.

Each of the subjects identified above as having an acute lung injury or insult, such as ARDS or pneumonia, or likely to develop an acute lung injury or insult, and those that subsequently develop other conditions, such as sepsis (e.g., infectious sepsis or sterile sepsis), can be treated by the methods of the invention.

Therapeutic Methods

The methods of the invention involve administering inter-alpha inhibitor proteins (IαIps) (e.g., inter-alpha inhibitor (IαI) and/or pre-alpha inhibitor (PαI)) or a composition containing IαIps (e.g., IαI and/or PαI) to a subject having ARDS or pneumonia, a subject likely to develop ARDS or pneumonia, a subject with sterile sepsis associated with ARDS, or a subject having sepsis (e.g., infectious sepsis or sterile sepsis) associated with ARDS or pneumonia. IαIps can be administered to a subject having or likely to develop acute respiratory failure (ARF). ARDS can include the 2012 Berlin definition or the 1994 AECC definition. Pneumonia can include hospital-acquired pneumonia (HAP), healthcare-associated pneumonia (HCAP), nursing home-acquired pneumonia (NHAP), ventilator-associated pneumonia (VAP), and community-acquired pneumonia (CAP), such as severe community acquired pneumonia (sCAP). Subjects in need of treatment can be identified using the clinical and symptomatic criteria described herein, or other approaches known in the art.

The methods of the invention can extend the period that the subject can be treated prior to developing sepsis (including infectious sepsis or sterile sepsis), SIRS, or organ failure, thereby prolonging the life span of the subject and/or the treatment window for the subject; for example, by minutes (e.g., 30 to 60 minutes or more), hours (e.g., 1, 2, 3, 4, 5, 10, 15, 20, or 24 hours or more), days (e.g., 1, 2, 3, 4, 5, 6, or 7 days or more), or weeks (e.g., 1, 2, 3, or 4 or more weeks). The methods may reduce the hospitalization time of the subject (e.g., by 1%, 5%, 10%, 20%, 25%, 30%, 40%, 50%, 60%, 70%, 80%, 90%, 95%, 99%, or more). For example, the patient may be discharged from the hospital 1-10 hours, 1-7 days, or 1-2 weeks sooner than a patient that is not treated with IαIps. In some cases, the methods can reduce the likelihood of death of the subject (e.g., by 1%, 5%, 10%, 20%, 25%, 30%, 40%, 50%, 60%, 70%, 80%, 90%, 95%, 99%, or more), relative to an untreated subject having the same condition.

The methods can include predicting a response to treatment by IαIps (e.g., IαI and/or PαI) that includes assaying a sample obtained from a subject to detect the level of IαIps. Any suitable approach to determine the level of IαIps may be used, for example, enzyme-linked immunosorbent assay (ELISA), western blotting, or mass spectrometry. The subject in need of treatment can be identified as having decreased levels of IαIps (e.g., IαI and/or PαI) as compared to a healthy subject. Measuring the levels of the IαIps allows for identification of a subject that may respond favorably to administration of IαIps (e.g., IαI and/or PαI) and/or compositions thereof.

The methods of treating and reducing the likelihood of developing ARDS and/or pneumonia can include restoring the levels of IαIps (e.g., IαI and/or PαI) in the lung tissue of a subject to a level corresponding to that of a healthy subject. A healthy subject may be one that does not have ARDS (e.g., ARF) or pneumonia (e.g., CAP (e.g., sCAP), HAP, HCAP, VAP, or NHAP). The dose of IαIps (e.g., IαI and/or PαI) administered to a subject can be sufficient to restore the level of IαIps (e.g., IαI and/or PαI) to the level of a healthy subject. The methods can also include administering IαIps (e.g., IαI and/or PαI) to a level that exceeds that of a healthy subject. In some instances, the level of IαI or PαI of a healthy subject is about 500 mg/L to about 1200 mg/L (e.g., about 500 mg/L, about 600 mg/L, about 700 mg/L, about 800 mg/L, about 900 mg/L, about 1000 mg/L, about 1100 mg/L, or about 1200 mg/L) of circulating IαI and/or PαI.

A subject may also be identified as having ARDS or pneumonia or in need of treatment for ARDS and/or pneumonia by detecting the level of one or more biomarkers associated with ARDS and/or pneumonia. For example, the method may include measuring the level of one or more biomarkers selected from IαIps (e.g., IαI and/or PαI), histone (e.g., extracellular histone), histone/PαI, histone/IαI, histone IαI/PαI complexes, TNF-alpha, IL-6, IL-10, IL-1, IL-1ra, IL1B, IL-8, MCP-1, MIP-2, C-reactive protein (CRP), procalcitonin (PCT), cytokine-induced neutrophil chemoattractant/KC, UTI, complement components (e.g., C1, C2, C3 (e.g., C3a and C3b), C4 (e.g., C4b), C5 (e.g., C5a and C5b), C6, C7, C8, C9, membrane attack complex, Factor B, Factor D, MASP-1, and MASP-2), or fragments thereof. The method can include measuring the protein level or the nucleic acid level of one or more of these biomarkers.

For example, with respect to ARDS, the level of one or more biomarkers selected from IαIps (e.g., IαI and/or PαI), histone (e.g., extracellular histone), histone/PαI, histone/IαI, histone IαI/PαI complexes, TNF-alpha, IL-6, IL-10, IL-1, IL-1ra, IL1B, IL-2, IL-4, IL-8, IL-15, MCP-1, MIP-2, CRP, PCT, cytokine-induced neutrophil chemoattractant/KC, UTI, complement components (e.g., C1, C2, C3 (e.g., C3a and C3b), C4 (e.g., C4b), C5 (e.g., C5a and C5b), C6, C7, C8, C9, membrane attack complex, Factor B, Factor D, MASP-1, and MASP-2), or fragments thereof, may be changed (e.g., increased or decreased) relative to a reference level. Appropriate levels for biomarkers associated with ARDS are known in the art. Exemplary, non-limiting levels of biomarkers associated with ARDS, which may be indicative of the presence and/or severity of ARDS, are provided by Tzouvelekis et al., *Respir. Res.* 6(1):62, 2005, which is incorporated herein by reference in its entirety.

For example, the level of TNF-alpha associated with ARDS may be about 400 pg/ml or greater. The level of IL-1 B associated with ARDS can be about 400 pg/ml or greater. The level of IL-2 associated with ARDS can be about 200 pg/ml or greater. In other instances, the level of IL-2 associated with ARDS can be about 173 pg/ml or greater (see, e.g., Agouridakis et al., *Eur. J. Clin. Invest.* 32(11): 862-7, 2002). The level of IL-4 associated with ARDS can be about 200 pg/ml or greater. The level of IL-6 associated with ARDS can be about 400 pg/ml or greater. The level of IL-8 associated with ARDS can be about 400 pg/ml or greater. The level of IL-15 associated with ARDS can be about 250 pg/ml or greater. The level of a biomarker for ARDS can be measured in any suitable biological sample, for example, blood (e.g., whole blood, plasma, or serum), bronchial lavage fluid (BALF), sputum, urine, cerebrospinal fluid (CSF), a tissue biopsy, and the like. Any of the preceding levels may be a plasma level.

With respect to pneumonia, the level of one or more biomarkers selected from IαIps (e.g., IαI and/or PαI), histone (e.g., extracellular histone), histone/PαI, histone/IαI, histone IαI/PαI complexes, TNF-alpha, IL-6, IL-10, IL-1, IL-1ra, IL1B, IL-8, MCP-1, MIP-2, CRP), procalcitonin (PCT), cytokine-induced neutrophil chemoattractant/KC, UTI, complement components (e.g., C1, C2, C3 (e.g., C3a and C3b), C4 (e.g., C4b), C5 (e.g., C5a and C5b), C6, C7, C8, C9, membrane attack complex, Factor B, Factor D, MASP-1, and MASP-2), or fragments thereof may be changed (e.g., increased or decreased) relative to a reference level. Appropriate levels for biomarkers associated with pneumonia are known in the art. Exemplary, non-limiting levels of biomarkers associated with pneumonia (e.g., CAP or sCAP), which may be indicative of the presence and/or severity of pneumonia, are provided by Seligman et al., *Clinics* 67(11):1321-1325, 2012 and Mira et al., *Crit. Care.* 12(Suppl. 6):S5, 2008, which are incorporated herein by reference in its entirety. Levels of IαIps associated with sepsis whose cause of sepsis is CAP are provided by Opal et al., *Crit. Care Med.* 2007; 35(2); 387-392, which is incorporated herein by reference in its entirety. For example, the level of PCT in healthy patients is usually undetectable or low, and is typically less than 0.1 ng/ml in serum. The level of PCT associated with pneumonia may be, for example, greater than about 0.1 ng/ml, e.g., from about 0.1 ng/ml to about 2 ng/ml. In other cases, the level of PCT may be greater than about 2 ng/ml (e.g., about 2 ng/ml, about 3 ng/ml, about 4 ng/ml, about 5 ng/ml, about 10 ng/ml, or greater). The level of CRP in healthy patients is typically less than about 3 mg/L. In some instances, the level of CRP associated with pneumonia may be greater than about 10 mg/L (e.g., about 10 mg/L, about 11 mg/L, about 12 mg/L, about 13 mg/L, about 14 mg/L, about 15 mg/L, or greater). The level of a biomarker for pneumonia can be measured in any suitable biological sample, for example, blood (e.g., whole blood, plasma, or serum), bronchial lavage fluid (BALF), sputum, urine, cerebrospinal fluid (CSF), a tissue biopsy, and the like. Any of the preceding levels may be a serum level.

The methods of the invention can also include monitoring the progress of a subject being treated with IαIps (e.g., IαI and/or PαI) by determining the pre-treatment level of IαIps (e.g., IαI and/or PαI); administering a therapeutically effective amount of IαIps (e.g., IαI and/or PαI), a composition thereof, and/or a secondary treatment to the subject; and determining the level of IαIps (e.g., IαI and/or PαI) in the subject after an initial period of treatment with the IαIps. An increase in the level of IαIps in the subject following treatment with IαIps (e.g., IαI and/or PαI) indicates that the subject is likely to have a favorable clinical response to treatment with IαIps, a composition thereof, or a combination thereof with a secondary treatment. A decrease or plateau in a detectable level of IαIps (e.g., IαI and/or PαI) can indicate that a subject may benefit from continued administration of IαIps or an increase in the dosage of IαIps administered to the subject.

The progress of a patient following treatment with an IαIp(s), or a co-administered secondary treatment, can be monitored and assessed by measuring the level of one or more biomarkers, e.g., inflammatory factors (e.g., TNF-alpha, IL-6, C5a, damage-associated molecular patterns (DAMPs), ERK, NF-κB levels, increased IL-10, and/or decreased serine proteases) as indicators of treatment efficacy. The administration of IαIps (e.g., IαI and/or PαI) to the subject may reduce the physiological response of the subject to cytokines (e.g., TNF-alpha) or free radicals. IαIps (e.g., IαI and PαI) may down-regulate pro-inflammatory mediators such as TNF-alpha and/or IL-6; up-regulate anti-inflammatory mediators such as IL-10; inhibit serine proteases such as trypsin, chymotrypsin, elastase, plasmin, granzyme K, preprotein convertase furin; block complement activation (e.g., C5a); block endogenous damage signals (DAMPs) such as extracellular histones; inhibit endothelial inflammation such as that caused by ERK/NF-κB pathways; and/or bind virtonectin and/or other matrix proteins in extracellular matrix, thereby promoting epithelial and/or endothelial repair via cellular proliferation and/or migration; and/or downregulation of adhesion factors such as ICAM, VCAM, and selectins, thereby reducing extravasation of immune cells into the tissues. Reductions in the level of one or more of the inflammatory factors (e.g., TNF-alpha, IL-6, C5a, DMAPs, ERK, and NF-κB levels) and/or increases in the level of IL-10, relative to an untreated ARDS and/or pneumonia patient, indicate treatment efficacy with the IαIps (s), or a co-administered secondary treatment.

Any of the methods described herein can further involve reducing inflammation and fluid in lung tissue and alveolar lung tissue.

IαIps (e.g., IαI and PαI) can reach sites of tissue injury via extravasation, and modify inflammatory and reparative processes when administered to the subject, such as restoring columnar epithelial structure and reducing abnormal nuclei in the airways of the lung.

In some instances, the methods of the invention reduce the need for ventilation of the subject, for example, by days (e.g., 1, 2, 3, 4, 5, 6, or 7 days), weeks (e.g., 1, 2, 3, or 4 weeks), or months (e.g., 1, 2, 3, 4, 5, 6, 7, 8, 9, 10, or 12 months) relative to untreated patients.

The methods of the invention described above can include the administration of IαI and PαI as the IαIps. In addition, one or more of bikunin, H4, and H5 can be administered alone or in combination with IαI and PαI as the IαIps.

Administration

IαIps (e.g., IαI and/or PαI), or a composition containing such proteins and a pharmaceutically acceptable excipient, diluent, or carrier, can be administered to the subject by any suitable route, including, for example, parenterally, by inhalation spray, topically, nasally, buccally, by oral administration, inhalation, suppository, or by injection. Administration by injection includes, for example, intravenous, intraperitoneal, subcutaneous, intracutaneous, intramuscular, intraarticular, intraarterial, intrasynovial, intrasternal, intrathecal, intralesional and intracranial injection. If the patient is hospitalized, the preferred method of administration is by intravenous injection.

The IαIps (e.g., IαI and/or PαI) or the composition containing such proteins may be administered to the subject one or more times every 1, 2, 3, 4, 5, 6, 8, 12, or 24 hours; one or more times every 1, 2, 3, 4, 5, or 6 days; or one or more times every 1, 2, 3, or 4 weeks. In other cases, the IαIps (e.g., IαI and/or PαI) or the composition containing such proteins are administered as a continuous infusion.

The compositions may be administered to the subject at least 10, 15, 20, 30, 60, or 120 minutes before an insult or injury to the lungs as described herein (e.g., a surgery or use of a ventilator). In other instances, the compositions may be administered to the subject at least 10, 15, 20, 30, 60, or 120 minutes after an insult or injury to the lungs as described herein (e.g., a surgery or use of a ventilator).

The compositions may also be administered upon diagnosis of ARDS or pneumonia or development of complications from ARDS or pneumonia (e.g., sepsis (e.g., infectious sepsis or sterile sepsis) or organ failure.

Dosages

A pharmaceutically acceptable composition of the invention includes IαIps (e.g., IαI and/or PαI) in a dosage known in the art (see, e.g., U.S. Pat. No. 7,932,365, International Patent Application Publication No. WO2009154695, and U.S. Patent Application Publication No. 2009/0190194, each of which is incorporated herein by reference in its entirety). For example, compositions of the invention can be administered in a dosage ranging from about 1 mg/kg to 50 mg/kg, preferably dosages between 10 mg/kg and 30 mg/kg. The dose can be administered one or more times every 1, 2, 3, 4, 5, 6, 8, 12, or 24 hours, every 1, 2, 3, 4, 5, or 6, days, or every 1, 2, 3, or 4 weeks, or as needed. Lower or higher doses than those recited above may be advantageous. Specific dosage and treatment regimens for any particular subject will depend upon a variety of factors, including the activity of the specific composition employed, the age, body weight, general health status, sex, diet, time of administration, rate of excretion, drug combination, the severity and course of the disease (e.g., the patient's condition and/or symptoms), the subject's disposition to the disease, and the judgment of the treating medical professional (e.g., the physician). The IαIps may be combined with a carrier material to produce a single dosage form.

Upon improvement of the patient's condition, a maintenance dose of an IαIp composition or combination therapy may be administered, if necessary. Subsequently, the dosage or frequency of administration, or both, may be reduced, as a function of the reduction in symptoms, to a level at which the improved condition is retained. When the symptoms have been alleviated to a desired level, treatment may cease. Subjects may, however, require intermittent treatment on a long-term basis upon any recurrence of disease symptoms. Improvement of the condition may also be judged based upon the level of IαI in a biological sample derived from the patient (e.g., blood (e.g., whole blood, plasma, or serum), bronchial lavage fluid (BALF), sputum, urine, cerebrospinal fluid (CSF), or a tissue biopsy (e.g., a liver biopsy).

Formulations

The invention provides methods of treating or reducing the likelihood of developing ARDS or pneumonia that involve administration of IαIps (e.g., IαI and/or PαI), a composition that includes IαIps (e.g., IαI and/or PαI) and a pharmaceutically acceptable excipient, carrier, or diluent, or such compositions combined with a secondary treatment, as is described herein. The compositions can be formulated as a solid or a liquid. The compositions can be formulated for administration by any suitable means including those described herein.

Injectable forms of IαIps for administration are particularly preferred. IαIps and compositions containing the same may be formulated for intravenous, intraperitoneal, subcutaneous, intracutaneous, intramuscular, intraarticular, intraarterial, intrasynovial, intrasternal, intrathecal, intralesional and intracranial injection or infusion techniques. The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, TWEEN® 80) and suspending agents. The sterile injectable preparation may also be a sterile injectable solution or suspension in a non-toxic parenterally acceptable diluent or solvent. Among the acceptable vehicles and solvents that may be employed are mannitol, water, Ringers solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as the TWEEN® or SPAN® ranges and/or other similar emulsifying agents or bioavailability enhancers which are commonly used in the manufacture of pharmaceutically acceptable solid, liquid, or other dosage forms may also be used for the purposes of formulation.

The compositions may also be formulated for oral administration in any orally acceptable dosage form including, but not limited to, capsules, tablets, emulsions and aqueous suspensions, dispersions and solutions. For the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase combined with emulsifying and/or suspending agents. If desired, certain sweetening and/or flavoring and/or coloring agents may be added.

For preparing solid compositions, such as tablets, the IαIps may be mixed with a pharmaceutical excipient to form a solid pre-formulation composition containing a homogeneous mixture. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation can then be subdivided into unit dosage forms of the type described above containing from, for example, 1 mg/kg to about 50 mg/kg of IαIps (e.g., IαI and/or PαI). The solid pre-formulation can contain about 10 mg/kg to 30 mg/kg of IαIps (e.g., IαI and/or PαI).

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable aqueous or organic solvents, or mixtures thereof, and powders. The liquid or solid compositions may contain suitable pharmaceutically acceptable excipients as described herein and/ or known in the art. The compositions can be administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Topical administration of the compositions is useful when the desired treatment involves areas or organs readily accessible by topical application. For application topically to the skin, the composition should be formulated with a suitable ointment containing the active components suspended or dissolved in a carrier. Carriers for topical administration of the compositions of this invention include, but are not limited to mineral oil, liquid petroleum, white petroleum, propylene glycol, polyoxyethylenepolyoxypropylene composition, emulsifying wax and water. Alternatively, the pharmaceutical composition can be formulated with a suitable lotion or cream containing the active composition suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol, and water.

The pharmaceutical compositions may also be administered in the form of suppositories for rectal administration. These compositions can be prepared by mixing a composition of this invention with a suitable non-irritating excipient which is solid at room temperature but liquid at the rectal temperature and therefore will melt in the rectum to release the active components. Such materials include, but are not limited to, cocoa butter, beeswax and polyethylene glycols. Topically-transdermal patches are also included in this invention.

The compositions administered to a subject can be in the form of one or more of the pharmaceutical compositions described above. These compositions can be sterilized by conventional sterilization techniques or may be sterile filtered. Aqueous solutions can be packaged for use as is, or lyophilized, the lyophilized preparation being combined with a sterile aqueous carrier prior to administration.

Pharmaceutically acceptable excipient, carriers, and diluents that may be used in the compositions may include, but are not limited to, ion exchangers, alumina, aluminum stearate, lecithin, self-emulsifying drug delivery systems (SEDDS) such as da-tocopherol polyethyleneglycol 1000 succinate, surfactants used in pharmaceutical dosage forms such as TWEEN® surfactants or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Other delivery systems can include time-release, delayed release or sustained release delivery systems. Such systems can avoid repeated administrations of compositions of the invention, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactide-glycolide), copolyoxalates, polycaprolactones, polyesteramides, polyorthoesters, polyhydroxybutyric acids, such as poly-D-(−)-3-hydroxybutyric acid (European Patent No. 133, 988), copolymers of L-glutamic acid and gamma-ethyl-L-glutamate (Sidman, K. R. et al., Biopolymers 22: 547-556), poly (2-hydroxyethyl methacrylate) or ethylene vinyl acetate (Langer, R. et al., J. Biomed. Mater. Res. 15:267-277; Langer, R. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono- di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832, 253, and 3,854,480.

The proportion or concentration of IαIps (e.g., IαI and/or PαI) in the composition can vary depending upon a number of factors including dosage, chemical characteristics (e.g., hydrophobicity), and the route of administration. The IαIps (e.g., IαI and/or PαI) may be present in the composition in a physiological proportion. Physiological proportions may be, for example, the proportions found in a person or animal that is healthy and/or the ratio of IαI and PαI that appears naturally in human plasma. Physiological proportions are typically from between about 60% to about 80% IαI and between about 20% to about 40% PαI. However, it is to be understood that physiological proportions may vary from these ranges, for example, due to normal variation in genetic makeup of subjects.

IαIps (e.g., IαI and/or PαI) or compositions thereof can have a half-life of, for example, greater than about 1, 1.5, 2, 2.5, 3, 3.5, 4, 4.5, 5, 7.5, or 10 hours. IαIps (e.g., IαI and/or PαI) or compositions thereof can have a half-life of greater than about 5 hours or, preferably, greater than about 10 hours. Longer half-lives are preferred, for example, because fewer doses are required to be administered to a subject over time.

The pH of the compositions typically will be between about 3 and about 11, for example, between about 5 and 9, between about 6 and 7, or between about 7 and 8. The use of certain of the foregoing excipients, carriers, or stabilizers may result in the formation of pharmaceutical salts.

Purity of Inter-alpha Inhibitor Proteins and Methods of Manufacture

IαIps (e.g., IαI and/or PαI) for use in the compositions of the invention can be obtained from, e.g., human plasma and blood by methods known in the art (See, e.g., U.S. Pat. No. 9,139,641, which is incorporated herein by reference in its entirety).

In part, the IαIps can be obtained at a purity of 80% to 100% (e.g., about 80%, about 85%, about 90%, about 95%, about 96%, about 97%, about 98%, about 99%, or about 100%) from a natural source (e.g., blood) and used to prepare a composition of the invention (see, e.g., U.S. Pat. No. 7,932,365, which is incorporated herein by reference in its entirety).

The compositions may include any suitable IαIp, for example, IαI, PαI, a heavy chain, a light chain, or any combination thereof. For example, the composition may include IαI, PαI, and/or bikunin. In some cases, the composition may include IαI and PαI. The heavy chain can be H1, H2, H3, H4, or H5. The light chain can be bikunin.

Combination Therapies

The methods of the invention also include administering or co-administering a second treatment in addition to IαIps (e.g., IαI and/or PαI) or a composition thereof for the treatment of ARDS or pneumonia. For example, the second treatment may include administering to the subject an antibiotic agent, an antiviral agent, an antifungal agent, an antiparasitic agent, an anti-inflammatory agent, a bronchodilator agent, a complement inhibitor, a vasopressor, a sedative, or mechanical ventilation.

When the method includes administering a combination of IαIps (e.g., IαI and/or PαI), or a composition including IαIps (e.g., IαI and/or PαI) and a pharmaceutically acceptable excipient, diluent, or carrier, and one or more second treatment agents, each agent is present at a dosage level of between about 1 to 100%, and more preferably between about 5 to 95%, of the dosage normally administered in a monotherapy regimen. The agent(s) of the second treatment may be administered separately, as part of a multiple dose regimen, from the IαIps (e.g., IαI and/or PαI) or the composition thereof. The IαIps and agent(s) of the second treatment can be administered simultaneously or sequentially in any order. Alternatively, the agent(s) of the second treatment may be part of a single dosage form, e.g., mixed together with the IαIps (e.g., IαI and/or PαI) in a single composition.

Exemplary agents that can be administered in combination with IαIps (e.g., IαI and/or PαI) or compositions thereof are discussed below.

Antibiotic Agents

The second treatment may include an antibiotic agent that is used to treat a bacterial infection. Non-limiting examples of antibiotic agents include amoxicillin, penicillin, doxycycline, clarithromycin, benzylpenicillin, azithromycin, daptomycin, linezolid, levofloxacin, moxifloxacin, gatifloxcin, gentamicin, macrolides, cephalosporins, azithromycin, ciprofloxacin, cefuroxime, amoxillin-potassium clavulanate, erythromycin, sulfamethoxazole-trimethoprim, doxycycline monohydrate, cefepime, ampicillin, cefpodoxime, ceftriaxone, cefazolin, erythromycin ethylsuccinate, meropenem, piperacillin-tazobactam, amikacin, erythromycin stearate, cefepime in dextrose, doxycycline hyclate, ampicillin-sulbactam, ceftazidime, gemifloxacin, gentamicin sulfate, erythromycin lactobionate, imipenem-cilastatin, cefoxitin, cefditoren pivoxil, ertapenem, doxycycline-benzoyl peroxide, ampicillin-sulbactam, meropenem, cefuroxime, cefotetan, piperacillin-tazobactam, broad-spectrum fluoroquinolones (which may be used, for example, to treat pneumonia caused by atypical pathogens such as *Mycoplasma pneumoniae* or *Chlamydophila pneumoniae*), and others known in the art.

Antiviral Agents

The second treatment may include an antiviral agent that is used to treat a viral infection. Non-limiting examples of antiviral agents include zanamivir, oseltamivir, permivir, ribavirin, acyclovir, ganciclovir, foscarnet, cidofovir, and others known in the art.

Antifungal Agents

The second treatment may include an antifungal agent that is used to treat a fungal infection. Non-limiting examples of antifungal agents include amphotericin, caspofungin, voriconazole, itraconazole, posaconazole, fluconazole, flucytosine, and others known in the art.

Antiparasitic Agents

The second treatment may include an antiparastic agent that is used to treat a parasitic infection (e.g., a parasitic protozoan infection. Non-limiting examples of antiparasitic agents include nitazoxanide, melarsoprol, eflornithine, metronidazole, tinidazole, miltefosine, mebendazole, pyrantel pamoate, thiabendazole, diethylcarbamazine, ivermectin, albendazole, praziquantel, rifampin, and others known in the art.

Anti-Inflammatory Agents

The second treatment may include an anti-inflammatory agent that is used to treat or reduce inflammation. Non-limiting examples of anti-inflammatory agents include corticosteroids, statins, steroids, nonsteroidal anti-inflammatory drugs, glucocorticoids, and others known the art.

Brochodilators

The second treatment may include a bronchodilator that is used to relax the bronchial muscles allowing airways to be larger and air to pass through the lungs. Non-limiting examples of bronchodilators include beta 2 agonists, xanthines, ipratropium, oxitropium, muscarinic receptor antagonists, ipratropium, oxitropium, theophylline, theobromine, caffeine, salbutamol, isoproterenol, albuterol, levalburerol, pirbuterol, metaproterenol, terbutaline, salmeterol, formoterol, and others known in the art.

Vasopressors

The second treatment may include a vasopressor that causes vasoconstriction and/or an increase in blood pressure. Non-limiting examples of vasopressors include epinephrine, isoproterenol, phenylephrine, norepinephrine, dobutamine, ephedrine, droxidopa, and others known in the art.

Sedatives

The second treatment may include a sedative. Non-limiting examples of sedatives include propofol, diprivan, morphine, fentanyl, midazolam, lorazepam, precede, infumorph, dexmedetomidine, alfentanil, and others known in the art.

Complement Inhibitors

The second treatment may include an inhibitor of complement activation. The composition may inhibit activation of one or more complement components such as C1, C2, C3 (e.g., C3a and C3b), C4 (e.g., C4b), C5 (e.g., C5a and C5b), C6, C7, C8, C9, membrane attack complex, Factor B, Factor D, MASP-1, and MASP-2, or fragments thereof. The complement inhibitors may include protease inhibitors such as C1-INH and Rhucin/rhC11NH, soluble complement regulators such as sCR1/TP10, CAB-2/MLN-2222, therapeutic antibodies such as eculizumab/SOLIRIS®, Pexelizumna, ofatumumab, complement component inhibitors such as compstatin, receptor antagonists such as PMX-53 and rhMBL.

Assays

Therapeutic efficacy can optionally be assayed by measuring, for example, the biological function of the treated tissue or organ (e.g., lung). Such methods are standard in the art. For example, lung function is assayed using spirometry, lung volume, and diffusion capacity tests. Other methods for assaying organ function are known to the skilled artisan and are described, The methods for treating a subject for ARDS or pneumonia can include the steps of determining the pre-treatment levels of IαIps (e.g., IαI and/or PαI); and administering a therapeutically effective amount of IαIps to the subject. Pre-treatment levels of IαIps (e.g., IαI and/or PαI) are the levels of the proteins in the subject prior to the first administration of IαIps (e.g., IαI and/or PαI). Post-treatment levels are the levels of IαIps (e.g., IαI and/or PαI) measured after administration of IαIps. The methods include determining the post-treatment levels of one or more of IαI and PαI after an initial period of treatment with IαI and/or PαI. A modulation in the level of IαI and/or PαI is an indication that the treatment is producing a favorable clinical response.

The level of IαIps (e.g., IαI and/or PαI) or other biomarkers described herein may be determined, for example, by immunological methods. For example, IαI and/or PαI complexes and/or other biomarkers can be detected and/or measured by a variety of detection methods including, for example, gas phase ion spectrometry methods, optical methods, electrochemical methods, atomic force microscopy, radio frequency methods, surface plasmon resonance, ellipsometry, and immunological methods.

Immune cells can be measured using any suitable method, for example, blood tests (e.g., microscopic analysis), flow cytometry, and others known in the art.

An immunoassay can be used to detect and analyze IαIps (e.g., IαI and PαI) and/or other biomarker proteins in a sample. This method can include: (a) providing an antibody that specifically binds to IαI and/or PαI; (b) contacting a sample with the antibody; and (c) detecting the presence of a complex of the antibody bound to the proteins in the sample. Suitable antibodies for use of the invention include, MAb 69.31, MAb 69.26, anti-IαIp polyclonal antibody, and anti-bikunin monoclonal or polyclonal antibody.

The following examples are intended to illustrate, rather than limit, the invention.

EXAMPLES

Example 1

Treatment of Patient Having Pneumonia

A 65-year old male presents to the hospital. The patient explains that he cannot breathe very well, his breaths are short and rapid, and he feels like he is gasping for air. The patient further complains of sharp chest pain and coughing. Upon examination, the clinician notes that the patient has diminished vital signs, a fever, and bluish coloring of his nail beds. The clinician also listens to the patient's lungs (e.g., using a stethoscope) while the patient inhales and exhales. The clinician hears crackles and other noises in the lungs. At this point, the patient is admitted to the hospital for suspected pneumonia, put on antibiotics, and then is sent for a chest X-ray. Upon examination of the patient's X-ray, the clinician confirms the initial diagnosis of pneumonia. The clinician also may order laboratory studies such as a blood culture, which may take 48 hours for the first read and 5 days for the full read. The levels of IαIps (e.g., IαI and/or PαI) in a biological sample derived from the patient (e.g., plasma) can also be determined. In this example, the level of IαIps is low, and a therapy that includes IαIps (e.g., IαI and/or PαI) is selected for the patient. In other examples, the patient's level of IαI proteins is normal (or even elevated), but IαIps may still be selected for the patient. If warranted by the patient's CURB-65 score, the patient can be sent to the intensive care unit (ICU).

To treat the pneumonia, the patient will be administered a therapeutically effective dose of IαIps (e.g., IαI and/or PαI). The effective dose that will be administered intravenously to the patient will be between 1 mg/kg to 50 mg/kg (e.g., 1, 2, 3, 4, 5, 6, 7, 8, 9, 10, 15, 20, 25, 30, 35, 40, 45, or 50 mg/kg), preferably between 10 mg/kg to 30 mg/kg. The patient will be further treated with a secondary treatment containing one or more antibiotic agents such as amoxicillin, penicillin, doxycycline, clarithromycin, benzylpenicillin, azithromycin, gentamicin, macrolides, or cephalosporins. The patient will be administered the composition one or more times every 1, 2, 3, 4, 5, 6, 8, 12, or 24 hours at the beginning of his therapy. As the patient progresses, the frequency of the therapy may decrease to one or more times every 1, 2, 3, 4, 5, or 6, days, or one or more times every 1, 2, 3, or 4 weeks. The patient will be provided with ventilation assistance should he have trouble breathing by himself.

Example 2

Treatment of Patient Having Chronic Obstructive Pulmonary Disorder

A 60 year old female patient suffering from chronic obstructive pulmonary disorder is scheduled to undergo a lung transplant. In preparation for her surgery, the patient is prescribed 5 mg/kg of IαIps (such as IαI and/or PαI) to be administered twice a day, every day for a week prior to the surgery.

Example 3

Treatment of Patient Having Acute Respiratory Distress Syndrome

A 65-year old male who has aspirated stomach contents presents to the hospital with diminished vital signs. Upon examination, the clinician notes that the patient has extreme shortness of breath, labored breathing, cough, and fever. The clinician orders a chest X-ray and the patient's chest imaging shows the presence of extensive bilateral infiltrates. The patient is diagnosed with acute respiratory distress syndrome (ARDS), which is confirmed by additional laboratory tests measuring the patient's $PaO_2/FiO_2$ levels, which is <200 mmHg.

The patient will be administered a therapeutically effective dose of IαIps (e.g., IαI and/or PαI). The effective dose that will be administered intravenously to the patient will be between 1 mg/kg to 50 mg/kg, preferably between 5 mg/kg to 15 mg/kg (e.g., 5, 6, 7, 8, 9, 10, 11, 12, 13, 14, or 15 mg/kg). The patient will be administered the composition one or more times every 1, 2, 3, 4, 5, 6, 8, 12, or 24 hours at the beginning of his therapy. As the patient progresses, the frequency of the therapy may decrease to one or more times every 1, 2, 3, 4, 5, or 6, days, or one or more times every 1, 2, 3, or 4 weeks. The patient will be provided with ventilation assistance should he have trouble breathing by himself.

Other Embodiments

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the invention.

Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

The invention claimed is:

1. A method of treating acute respiratory distress syndrome (ARDS) or pneumonia in a subject in need thereof comprising administering to the subject inter-alpha inhibitor proteins (IαIps), wherein the subject is an adult human with a ratio of partial pressure of arterial oxygen to fraction of inspired oxygen ($PaO_2/FiO_2$) of about 300 mm Hg or less, wherein the method comprises administering the IαIps to the subject prior to development of sepsis, wherein the IαIps comprise IαI and PαI, and wherein the IαI and PαI are in physiological proportions.

2. The method of claim 1, wherein:
   a) the ARDS or the pneumonia is caused by a bacterial infection;
   b) the subject has one or more symptoms of the ARDS comprising shortness of breath, cough, fever, rapid heart rate, low blood pressure, rapid breathing, chest pain, bluish coloring of nails, or bluish coloring of lips;
   c) the subject has one or more symptoms of the pneumonia comprising cough, fever, shaking chills, shortness of breath, wheezing, chest pain, headache, excessive sweating, clammy skin, loss of appetite, low energy, fatigue, confusion, muscle pain, muscle weakness, or inflammation;
   d) the ARDS comprises acute respiratory failure (ARF);
   e) the ARDS results from pneumonia, ventilation induced pneumonia, trauma, damage to the brain, a blood transfusion, babesiosis, lung contusion, lung transplant, aspiration of stomach contents, drug abuse, drug overdose, a burn, pancreatitis, near drowning, inhalation of chemical fumes, or administration of resuscitation fluid;
   f) g) the pneumonia comprises hospital-acquired pneumonia (HAP), health care-associated pneumonia (HCAP), nursing home-acquired pneumonia (NHAP), ventilator-associated pneumonia (VAP), or community-acquired pneumonia (CAP); or
   g) the pneumonia results from an infection of lung tissue.

3. The method of claim 2, wherein:
   a) the bacterial infection is caused by an antibiotic resistant bacteria;
   b) the ARDS results from inhalation of chemical fumes, and the chemical fumes are selected from the group consisting of smoke, phosgene, chlorine gas, acrolein, ammonia, ethylene oxide, formaldehyde, hydrogen chloride, hydrogen fluoride, hydrogen sulfide, methyl bromide, sodium azide, sulfur dioxide, cadmium fume, mercury fume, mustard gas, nickel carbonyl, oxides of nitrogen, and ozone;
   c) the ARDS results from administration of resuscitation fluid, and the resuscitation fluid comprises colloid solutions;
   d) the ARDS results from trauma, and the trauma is acidosis;
   e) the pneumonia comprises CAP and the CAP is severe CAP (sCAP); or
   f) the pneumonia results from an infection of lung tissue caused by a bacteria, a virus, a fungus, a parasite, or other microorganism.

4. The method of claim 1, wherein the method comprises:
   a) treating one or more symptoms of the ARDS comprising mild, moderate or severe hypoxemia as determined by Partial Pressure of arterial oxygen/Fraction of inspired oxygen ($PaO_2/FiO_2$) or positive end-expiratory pressure (PEEP), bilateral opacities, respiratory failure, shortness of breath, labored breathing, cough, fever, increased heart rate, low blood pressure, confusion, extreme tiredness, rapid breathing, organ failure, chest pain, bluish coloring of nails or lips, a change in the level of one or more inflammatory markers, or need for mechanical ventilation;
   b) treating one or more symptoms of the pneumonia comprising symptoms included in the CRB-65 test, the CURB-65 test, or the pneumonia severity index (PSI), cough, fever, shaking chills, shortness of breath, wheezing, chest pain, headache, excessive sweating, clammy skin, loss of appetite, low energy, fatigue, confusion, muscle pain, muscle weakness, or inflammation;
   c) reducing inflammation and/or promoting repair in lung tissue;
   d) reducing fluid in lung tissue;
   e) administering IαIps to the subject prior to organ failure in the subject;
   f) measuring the levels of IαIps in a biological sample derived from the subject prior to administration of the IαIps;
   g) measuring the levels of histones or histone/IαI/PαI complexes in a biological sample derived from the subject;
   h) restoring or exceeding the level of IαI and/or PαI in the lung tissue of the subject to that of a healthy subject;
   i) administering a single dose or multiple doses of the IαIps sufficient to restore or exceed the level of the IαIps in the lung tissue of the subject;
   j) neutralizing histones with the IαIps;
   k) administering a composition comprising the IαIps;
   l) administering the IαIps to the subject at least 10, 15, 20, 30, 60, or 120 minutes after a lung insult;
   m) measuring the level of one or more biomarkers associated with the ARDS or the pneumonia in a biological sample derived from the subject;
   n) administering a second treatment for the ARDS or the pneumonia; or
   o) administering an inhibitor of complement activation.

5. The method of claim 4, wherein:
   a) the one or more inflammatory markers is selected from the group consisting of TNF-alpha, interleukin 6 (IL-6), complement component 5a (C5a), damage-associated molecular patterns (DAMPs), extracellular-signal-regulated kinase (ERK), nuclear factor-kappa B (NF-κB), interleukin 10 (IL-10), and a serine protease;
   b) the change in the level of one or more inflammatory markers is an increase;
   c) the change in the level of one or more inflammatory markers is a decrease;
   d) the symptoms of the ARDS begin within 2 to 72 hours after a lung insult;

e) the lung tissue in which inflammation is reduced and/or repair is promoted or in which fluid is reduced is alveolar lung tissue;
f) the method comprises measuring the levels of IαI, PαI, an IαIp heavy chain, an IαIp light chain, or a combination thereof;
g) the single dose comprises about 1 mg/kg to about 50 mg/kg of the IαIps;
h) the composition comprises about 1 mg/kg to about 50 mg/kg of the IαI and PαI;
i) the biological sample derived from the subject is a blood sample, a urine sample, a sputum sample, or a bronchiolar lavage fluid sample;
j) the composition is administered to the subject one or more times every 1, 2, 3, 4, 5, 6, 8, 12, or 24 hours, every 1, 2, 3, 4, 5, or 6 days, or every 1, 2, 3, or 4 weeks;
k) the lung insult occurs as a result of radiation treatment, chemotherapy, exposure to high altitude, swimming, diving, or surgery;
l) the one or more biomarkers comprise histone, histone/PαI complexes, histone/IαI complexes, histone/IαI/PαI complexes, tumor necrosis factor alpha (TNF-α), IL-6, IL-10, interleukin 1 (IL-1), interleukin 1 receptor antagonist (IL-1ra), interleukin 1 beta (IL 1B), interleukin 8 (IL-8), monocyte chemoattractant protein 1 (MCP-1), macrophage inflammatory protein 2 (MIP-2), c-reactive protein (CRP), procalcitonin (PCT), cytokine-induced neutrophil chemoattractant/keratinocyte chemoattractant (KC), a complement component, or fragments thereof;
m) the second treatment comprises one or more of an antibiotic, an antiviral agent, an antifungal agent, an antiparasitic agent, an anti-inflammatory agent, a bronchodilator, a vasopressor, a sedative, or mechanical ventilation; or
n) administration of the IαIps
   i) inhibits activation of one or more complement components;
   ii) reduces the likelihood of death or hospitalization time for the subject; and/or
   iii) reduces the physiological response to inflammatory mediators selected from the group consisting of cytokines, chemokines, complement, and histones.

6. The method of claim 3, wherein:
a) the ARDS results from administration of resuscitation fluid, and the resuscitation fluid comprises colloid solutions, and the colloid solution comprises hydroxyethyl starch solution and/or albumin;
b) the pneumonia results from an infection of lung tissue caused by a bacteria, and the bacteria is an *Enterobacteriaceae* species (spp.), *Streptococcus pneumoniae, Staphylococcus aureus, Bacillus anthracis, Haemophilus influenzae, Klebsiella pneumoniae, Escherichia coli, Pseudomonas aeruginosa, Bordetella pertussis, Moraxella catarrhalis, Coxiella burnetii, Chlamydophila pneumoniae*, a *Legionella* spp., or *Mycoplasma pneumoniae*;
c) the pneumonia results from an infection of lung tissue and the infection is caused by a virus, and the virus is an influenza virus, parainfluenza, swine origin influenza, Respiratory syncytial virus, Human parainfluenza virus, an Adenovirus, a Metapneumovirus, Severe acute respiratory syndrome virus, herpes simplex virus (HSV), Varicella-zoster virus (VZV), measles virus, Rubella virus, Cytomegalovirus (CMV), smallpox virus, dengue virus, rhinovirus, bocavirus, or Middle East respiratory syndrome virus; or
d) the pneumonia results from an infection of lung tissue and the infection is caused by a fungus, and the fungus is *Histoplasma capsulatum, Coccidioides immitis, Coccidioides posadasii, Pneumocystis jirovecii, Blastomyces dermatitidis, Sporothrix schenckii, Cryptococcus neoformans, Cryptococcus gattii, Paracoccidioides brasiliensis*, a *Candida* spp., an *Aspergillus* spp., or a *Mucor* spp.

7. The method of claim 6, wherein:
a) the pneumonia results from an infection of lung tissue and the infection is caused by methicillin-resistant *Staphylococcus aureus* (MRSA);
b) the pneumonia results from an infection of lung tissue and the infection is caused by Legionella pneumophila; or
c) the pneumonia results from an infection of lung tissue and the infection is caused by an influenza virus A or an influenza virus B.

8. The method of claim 5, wherein:
a) the lung insult is or is caused by pneumonia, ventilation-induced pneumonia, trauma, damage to the brain, a blood transfusion, babesiosis, lung contusion, lung transplant, aspiration of stomach contents, drug abuse, drug overdose, a burn, pancreatitis, near drowning, inhalation of chemical fumes, lung transplant, a large volume of fluid used during post-trauma resuscitation, or infection of lung tissue;
b) the method comprises measuring the levels of IαI and/or PαI in the biological sample from the subject;
c) the composition of subpart h) comprises about 5 mg/kg to about 15 mg/kg of the IαI and and/or PαI;
d) the blood sample is whole blood, serum, plasma, or a combination thereof; or
e) the complement component biomarker is selected from the group consisting of complement component 1 (C1), complement component 2 (C2), complement component 3 (C3), complement component 3a (C3a), complement component 3b (C3b), complement component 4 (C4), complement component 4b (C4b), complement component 5 (C5), C5a, complement component 5b (C5b), complement component 6 (C6), complement component 7 (C7), complement component 8 (C8), complement component 9 (C9), membrane attack complex, Factor B, Factor D, mannan-binding lectin serine protease 1 (MASP-1), and mannan-binding lectin serine protease 2 (MASP-2).

9. The method of claim 8, wherein
the chemical fumes are selected from the group consisting of smoke, phosgene, acrolein, ammonia, ethylene oxide, formaldehyde, hydrogen chloride, hydrogen fluoride, hydrogen sulfide, methyl bromide, sodium azide, sulfur dioxide, cadmium fume, mercury fume, mustard gas, nickel carbonyl, oxides of nitrogen, ozone and chlorine gas.

10. The method of claim 1, wherein the subject exhibits:
a) decreased levels of IαI and/or PαI relative to a healthy subject;
b) increased levels of histones relative to a healthy subject; or
c) increased levels of histone/IαI/PαI complexes relative to an untreated subject.

11. The method of claim 10, wherein the level of IαI and/or PαI of a healthy subject is about 300 mg/L to about 1000 mg/L of circulating IαI and/or PαI.

12. The method of claim 4, wherein the composition:
a) further comprises a pharmaceutically acceptable excipient, diluent, or carrier, or an antibiotic agent, an antiviral agent, an antifungal agent, an anti-parasitic agent, an anti-inflammatory agent, a vasopressor, a sedative, a bronchodilator, or an inhibitor of complement activation;
b) is formulated as a solid, or liquid, or is formulated for inhalation, insufflation, nebulization, or injection, or is formulated for oral, rectal, topical, or intraperitoneal administration; or
c) has a half-life of greater than 1, 1.5, 2, 2.5, 3, 3.5, 4, 4.5, 5, 7.5, or 10 hours.

13. The method of claim 12, wherein:
a) the injection is intravenous injection;
b) the composition further comprises an antibiotic agent, and the antibiotic agent comprises amoxicillin, penicillin, doxycycline, clarithromycin, benzylpenicillin, azithromycin, daptomycin, linezolid, levofloxacin, moxifloxacin, gatifloxcin, gentamicin, macrolides, cephalosporins, azithromycin, ciprofloxacin, cefuroxime, amoxillin-potassium clavulanate, erythromycin, sulfamethoxazole-trimethoprim, doxycycline monohydrate, cefepime, ampicillin, cefpodoxime, ceftriaxone, cefazolin, erythromycin ethylsuccinate, meropenem, piperacillin-tazobactam, amikacin, erythromycin stearate, cefepime in dextrose, doxycycline hyclate, ampicillin-sulbactam, ceftazidime, gemifloxacin, gentamicin sulfate, erythromycin lactobionate, imipenem-cilastatin, cefoxitin, cefditoren pivoxil, ertapenem, doxycycline-benzoyl peroxide, ampicillin-sulbactam, meropenem, cefuroxime, cefotetan, or piperacillin-tazobactam;
c) the composition further comprises an antiviral agent, and the antiviral agent comprises zanamivir, oseltamivir, peramivir, ribavirin, acyclovir, ganciclovir, foscarnet, or cidofovir;
d) the composition further comprises an antifungal agent, and the antifungal agent comprises amphotericin, caspofungin, voriconazole, itraconazole, posaconazole, fluconazole, or flucytosine;
e) the composition further comprises an antiparasitic agent, and the antiparasitic agent comprises nitazoxanide, melarsoprol, eflornithine, metronidazole, tinidazole, miltefosine, mebendazole, pyrantel pamoate, thiabendazole, diethylcarbamazine, ivermectin, albendazole, praziquantel, or rifampin;
f) the composition further comprises an anti-inflammatory agent, and the anti-inflammatory agent comprises a corticosteroid, a statin, a steroid, a nonsteroidal anti-inflammatory drug, or a glucocorticoid;
g) the composition further comprises a bronchodilator, and the bronchodilator comprises a beta 2 agonist, a xanthine, ipratropium, oxitropium, a muscarinic receptor antagonist, ipratropium, oxitropium, theophylline, theobromine, caffeine, salbutamol, isoproterenol, albuterol, levalbuterol, pirbuterol, metaproterenol, terbutaline, salmeterol, or formoterol;
h) the composition further comprises a vasopressor, and the vasopressor comprises epinephrine, isoproterenol, phenylephrine, norepinephrine, dobutamine, ephedrine, or droxidopa; or
i) the composition further comprises a sedative, and the sedative comprises propofol, diprivan, morphine, fentanyl, midazolam, lorazepam, infumorph, dexmedetomidine, or alfentanil.

14. The method of claim 12, wherein the composition further comprises an inhibitor of complement activation and the composition inhibits activation of one or more complement components, and the complement components comprise C1, C2, C3, C4, or C5.

15. The method of claim 1, wherein the subject:
a) has the ARDS or the pneumonia;
b) is hospitalized;
c) requires ventilator-assisted breathing;
d) has one or more organ failures;
e) is identified as being in need of treatment using one or more of the following: chest imaging, arterial blood gas level, partial pressure of oxygen ($PaO_2$) levels, partial pressure of carbon dioxide ($PaCO_2$) levels, blood pH, pathogen specific test, or sputum evaluation;
f) is identified as having mild, moderate or severe hypoxemia as determined by $PaO_2/FiO_2$ or positive end-expiratory pressure (PEEP);
g) is identified as having bilateral opacities consistent with edema;
h) is identified as having confusion, blood urea nitrogen being equal to one more than 20 mg/dl, respiratory rate being equal to or greater than 30 breaths per minute, systolic blood pressure being less than 90 mm Hg, diastolic blood pressure being equal to or less than 60 mm Hg, or is 65 or older;
i) is identified as being a nursing home resident, having neoplastic disease, having a history of liver, heart, cerebrovascular, or renal disease, being in a state of altered mental state, having a respiratory rate greater than or equal to 30 breaths per minute, having a systolic blood pressure above 90 mmHg, having a temperature above 35° C. or greater than or equal to 40° C., having a pulse greater than or equal to 125/min, having an arterial pH less than 7.35, having a blood urea nitrogen greater than or equal to 30 ng/dl, having sodium levels being greater than 130 mmol/L, having glucose levels greater than or equal to 250 mg/dl or greater than 13.8 mmol/liter), having hematocrit values being less than 30%, having a partial pressure of oxygen less than 60 mm Hg, or by the presence of pleural effusion on X-ray; or
j) has undergone or is scheduled to undergo a lung transplant.

16. The method of claim 15, wherein:
a) the subject is hospitalized, and the hospitalized subject is in an intensive care unit;
b) the subject requires ventilator-assisted breathing, and the ventilator-assisted breathing is mechanical ventilator-assisted breathing;
c) the subject is identified as being in need of treatment using chest imaging, and the chest imaging is chest X-ray;
d) the subject has two or more organ failures; and/or
e) the subject has respiratory failure.

17. The method of claim 16, wherein:
a) the mechanical ventilator-assisted breathing is invasive or non-invasive mechanical ventilator-assisted breathing or is pressure-limited or volume-limited; and/or
b) the subject has failures of the liver failure, kidney, intestine, heart, or brain.

18. The method of claim 3, wherein
the IαIps are at about 80% to about 100% purity.

* * * * *

UNITED STATES PATENT AND TRADEMARK OFFICE
CERTIFICATE OF CORRECTION

PATENT NO. : 12,285,471 B2
APPLICATION NO. : 17/821713
DATED : April 29, 2025
INVENTOR(S) : Yow-Pin Lim et al.

Page 1 of 1

It is certified that error appears in the above-identified patent and that said Letters Patent is hereby corrected as shown below:

In the Claims

Column 27, Claim 2, Line 48, replace "f) g) the pneumonia comprises"
With --f) the pneumonia comprises--.

Column 28, Claim 4, Line 45, replace "i) neutralizing histones with the l$\alpha$lps;"
With --j) neutralizing histones with the l$\alpha$lps;--.

Column 30, Claim 8, Line 31, replace "to about 15 mg/kg of the l$\alpha$l and and/or P$\alpha$l;"
With --to about 15 mg/kg of the l$\alpha$l and P$\alpha$l;--.

Signed and Sealed this
Seventeenth Day of June, 2025

Coke Morgan Stewart
*Acting Director of the United States Patent and Trademark Office*